United States Patent
Cracchiolo et al.

(10) Patent No.: US 7,970,626 B2
(45) Date of Patent: Jun. 28, 2011

(54) FACILITATING PAYMENTS TO HEALTH CARE PROVIDERS

(75) Inventors: Christopher P. Cracchiolo, Manalapan, NJ (US); Jason S. Jagatic, Hoboken, NJ (US); Ahana M. Kalappa, New York, NY (US); Mark C. Keck, New York, NY (US); Shari Pincock, West Jordan, UT (US); Todd H. Reynders, Westfield, NJ (US); Sunil Sachdev, Forest Hills, NY (US)

(73) Assignee: Oltine Acquistitions NY LLC, Dover, DE (US)

( * ) Notice: Subject to any disclaimer, the term of this patent is extended or adjusted under 35 U.S.C. 154(b) by 0 days.

(21) Appl. No.: 11/275,403

(22) Filed: Dec. 29, 2005

(65) Prior Publication Data

US 2007/0011025 A1  Jan. 11, 2007

Related U.S. Application Data

(60) Provisional application No. 60/697,514, filed on Jul. 8, 2005.

(51) Int. Cl.
*G06Q 50/00* (2006.01)
*G06Q 10/00* (2006.01)

(52) U.S. Cl. .............................. 705/2; 705/4
(58) Field of Classification Search .............. 705/2–4
See application file for complete search history.

(56) References Cited

U.S. PATENT DOCUMENTS

| | | | |
|---|---|---|---|
| 4,491,725 A * | 1/1985 | Pritchard | 705/2 |
| 4,713,761 A * | 12/1987 | Sharpe et al. | 705/30 |
| 4,858,121 A | 8/1989 | Barber et al. | |
| 4,916,611 A * | 4/1990 | Doyle et al. | 705/2 |
| 5,235,507 A | 8/1993 | Sackler et al. | |
| 5,301,105 A | 4/1994 | Cummings, Jr. | |
| 5,532,464 A * | 7/1996 | Josephson et al. | 235/379 |
| 5,550,734 A * | 8/1996 | Tarter et al. | 705/2 |
| 5,583,760 A | 12/1996 | Klesse | |
| 5,704,044 A | 12/1997 | Tarter et al. | |
| 5,734,838 A | 3/1998 | Robinson et al. | |
| 5,740,425 A | 4/1998 | Povilus | |
| 5,826,243 A | 10/1998 | Musmanno et al. | |
| 5,832,447 A | 11/1998 | Rieker et al. | |
| 5,857,079 A | 1/1999 | Claus et al. | |
| 5,873,069 A | 2/1999 | Reuhl et al. | |
| 5,878,141 A | 3/1999 | Daly et al. | |

(Continued)

OTHER PUBLICATIONS

Alonso, Enhancing the fault tolerance of workflow management systems, Jul. 2000, Concurrency, IEEE, vol. 3, Issue 3, p. 74-81.*

(Continued)

*Primary Examiner* — Luke Gilligan
*Assistant Examiner* — Tran Nguyen
(74) *Attorney, Agent, or Firm* — Sterne, Kessler, Goldstein & Fox P.L.L.C.

(57) ABSTRACT

A computer-implemented method to facilitate a purchase comprising: receiving, at a first host computer, a request from a provider for payment authorization for a charge to a purchaser; examining a database coupled to the first host computer for information concerning the purchaser; providing the information concerning the purchaser to a second host computer associated with the provider; receiving at the first host computer information from a third host computer concerning a negotiated amount of the charge to the purchaser; tendering payment of the negotiated charge to the provider; and withdrawing an amount no greater than the negotiated amount of the charge from an account of the purchaser.

20 Claims, 10 Drawing Sheets

U.S. PATENT DOCUMENTS

Figure 1:
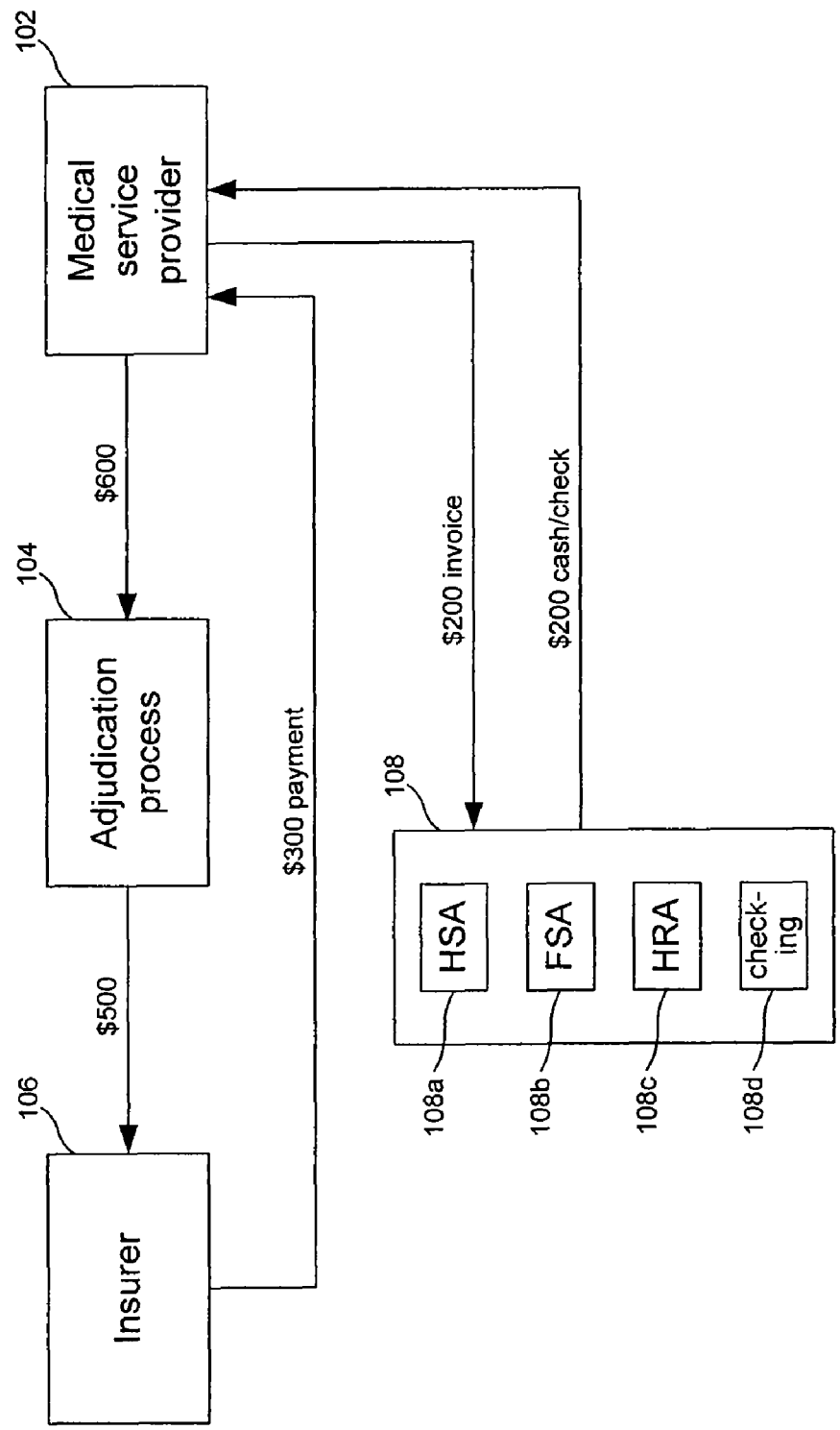

| | | |
|---|---|---|
| 5,903,830 A | 5/1999 | Joao et al. |
| 5,930,759 A | 7/1999 | Moore et al. |
| 5,945,653 A | 8/1999 | Walker et al. |
| 6,012,035 A | 1/2000 | Freeman, Jr. et al. |
| 6,042,005 A | 3/2000 | Basile et al. |
| 6,108,641 A * | 8/2000 | Kenna et al. .................. 705/35 |
| 6,112,986 A | 9/2000 | Berger et al. |
| 6,154,732 A | 11/2000 | Tarbox |
| 6,208,973 B1 | 3/2001 | Boyer et al. |
| 6,249,772 B1 | 6/2001 | Walker et al. |
| 6,292,786 B1 | 9/2001 | Deaton et al. |
| 6,339,766 B1 | 1/2002 | Gephart |
| 6,341,265 B1 | 1/2002 | Provost et al. |
| 6,343,271 B1 | 1/2002 | Peterson et al. |
| 6,343,279 B1 | 1/2002 | Bissonette et al. |
| 6,353,811 B1 | 3/2002 | Weissman |
| 6,386,450 B1 | 5/2002 | Ogasawara |
| 6,394,341 B1 | 5/2002 | Mäkipää et al. |
| 6,418,441 B1 | 7/2002 | Call |
| 6,422,462 B1 | 7/2002 | Cohen |
| 6,442,526 B1 | 8/2002 | Vance et al. |
| 6,442,532 B1 | 8/2002 | Kawan |
| 6,488,205 B1 | 12/2002 | Jacobson |
| 6,543,683 B2 | 4/2003 | Hoffman |
| 6,594,640 B1 | 7/2003 | Postrel |
| 6,601,761 B1 | 8/2003 | Katis |
| 6,615,190 B1 | 9/2003 | Slater |
| 6,637,649 B2 | 10/2003 | Walsh |
| 6,662,999 B1 | 12/2003 | Vancour et al. |
| 6,671,358 B1 | 12/2003 | Seidman et al. |
| 6,749,114 B2 | 6/2004 | Madani |
| 6,776,332 B2 | 8/2004 | Allen et al. |
| 6,820,058 B2 | 11/2004 | Wood et al. |
| 6,820,059 B2 | 11/2004 | Wood et al. |
| 6,879,959 B1 | 4/2005 | Chapman et al. |
| 6,898,598 B2 | 5/2005 | Himmel et al. |
| 6,932,268 B1 | 8/2005 | McCoy et al. |
| 6,947,900 B2 | 9/2005 | Giordano, III et al. |
| 6,999,943 B1 | 2/2006 | Johnson et al. |
| 7,039,593 B2 | 5/2006 | Sager |
| 7,072,842 B2 * | 7/2006 | Provost et al. .................. 705/4 |
| 7,097,098 B2 | 8/2006 | Roberts |
| 7,104,443 B1 | 9/2006 | Paul et al. |
| 7,133,840 B1 | 11/2006 | Kenna et al. |
| 7,158,955 B2 | 1/2007 | Diveley et al. |
| 7,174,302 B2 | 2/2007 | Patricelli et al. |
| 7,197,468 B1 | 3/2007 | Patricelli et al. |
| 7,213,750 B1 * | 5/2007 | Barnes et al. ................ 235/381 |
| 7,233,942 B2 | 6/2007 | Nye |
| 7,234,156 B2 | 6/2007 | French et al. |
| 7,249,097 B2 | 7/2007 | Hutchison et al. |
| 7,249,112 B2 | 7/2007 | Berardi et al. |
| 7,263,493 B1 | 8/2007 | Provost et al. |
| 7,268,667 B2 | 9/2007 | Beenau et al. |
| 7,268,668 B2 | 9/2007 | Beenau et al. |
| 7,333,937 B2 * | 2/2008 | Baldwin et al. .................. 705/2 |
| 7,346,522 B1 | 3/2008 | Baylor et al. |
| 7,380,707 B1 | 6/2008 | Fredman |
| 7,392,224 B1 | 6/2008 | Bauer et al. |
| 7,434,729 B2 | 10/2008 | Cracchiolo et al. |
| 7,493,266 B2 | 2/2009 | Gupta |
| 7,499,875 B1 | 3/2009 | May et al. |
| 7,566,000 B2 | 7/2009 | Agostino et al. |
| 7,624,026 B2 | 11/2009 | DiPiero et al. |
| 7,650,308 B2 | 1/2010 | Nguyen et al. |
| 7,739,131 B1 | 6/2010 | Luedtke |
| 2001/0001877 A1 | 5/2001 | French et al. |
| 2001/0014873 A1 | 8/2001 | Henderson et al. |
| 2001/0034618 A1 | 10/2001 | Kessler et al. |
| 2002/0016764 A1 | 2/2002 | Hoffman |
| 2002/0019885 A1 | 2/2002 | Sleeper |
| 2002/0035529 A1 | 3/2002 | Tooke |
| 2002/0087444 A1 | 7/2002 | DiPiero et al. |
| 2002/0099659 A1 | 7/2002 | Swentor |
| 2002/0116206 A1 | 8/2002 | Chatani |
| 2002/0128879 A1 | 9/2002 | Spears |
| 2002/0147678 A1 | 10/2002 | Drunsic |
| 2002/0174030 A1 | 11/2002 | Praisner et al. |
| 2002/0198831 A1 | 12/2002 | Patricelli et al. |
| 2002/0198833 A1 | 12/2002 | Wohlstadter |
| 2003/0018567 A1 | 1/2003 | Flitcroft et al. |
| 2003/0023498 A1 * | 1/2003 | Benton ........................ 705/26 |
| 2003/0023549 A1 | 1/2003 | Armes et al. |
| 2003/0033272 A1 | 2/2003 | Himmel et al. |
| 2003/0061153 A1 | 3/2003 | Birdsong et al. |
| 2003/0061358 A1 | 3/2003 | Piazza et al. |
| 2003/0065561 A1 | 4/2003 | Brown et al. |
| 2003/0065597 A1 | 4/2003 | Smith et al. |
| 2003/0069760 A1 | 4/2003 | Gelber |
| 2003/0088487 A1 | 5/2003 | Cheng et al. |
| 2003/0097331 A1 | 5/2003 | Cohen |
| 2003/0119554 A1 | 6/2003 | Horn |
| 2003/0126094 A1 | 7/2003 | Fisher et al. |
| 2003/0130948 A1 | 7/2003 | Algiene et al. |
| 2003/0135459 A1 | 7/2003 | Abelman et al. |
| 2003/0187695 A1 | 10/2003 | Drennan |
| 2003/0195769 A1 | 10/2003 | Francis |
| 2003/0195773 A1 | 10/2003 | Mahaffey |
| 2003/0200118 A1 | 10/2003 | Lee et al. |
| 2003/0216997 A1 | 11/2003 | Cohen |
| 2003/0225678 A1 | 12/2003 | Understein |
| 2004/0010449 A1 | 1/2004 | Berardi et al. |
| 2004/0010462 A1 | 1/2004 | Moon et al. |
| 2004/0049425 A1 | 3/2004 | Bakker et al. |
| 2004/0083183 A1 | 4/2004 | Hardesty et al. |
| 2004/0098328 A1 | 5/2004 | Grant et al. |
| 2004/0098351 A1 | 5/2004 | Duke |
| 2004/0117302 A1 | 6/2004 | Weichert et al. |
| 2004/0138999 A1 | 7/2004 | Friedman et al. |
| 2004/0238622 A1 | 12/2004 | Freiberg |
| 2004/0243464 A1 | 12/2004 | Beck |
| 2004/0249745 A1 | 12/2004 | Baaren |
| 2005/0015280 A1 | 1/2005 | Gabel et al. |
| 2005/0027607 A1 | 2/2005 | Pearson |
| 2005/0033677 A1 | 2/2005 | Birdsong et al. |
| 2005/0038740 A1 | 2/2005 | Ogilvie |
| 2005/0043992 A1 | 2/2005 | Cohagan et al. |
| 2005/0065873 A1 | 3/2005 | Hendrickson et al. |
| 2005/0075931 A1 | 4/2005 | Pearson |
| 2005/0080692 A1 | 4/2005 | Padam et al. |
| 2005/0098621 A1 | 5/2005 | de Sylva |
| 2005/0102181 A1 | 5/2005 | Scroggie et al. |
| 2005/0144071 A1 | 6/2005 | Monahan et al. |
| 2005/0144074 A1 | 6/2005 | Fredregill et al. |
| 2005/0149436 A1 | 7/2005 | Elterich |
| 2005/0216315 A1 | 9/2005 | Andersson |
| 2005/0256794 A1 | 11/2005 | Colby |
| 2005/0261968 A1 | 11/2005 | Randall et al. |
| 2005/0288964 A1 | 12/2005 | Lutzen et al. |
| 2006/0027647 A1 | 2/2006 | Deane et al. |
| 2006/0036523 A1 | 2/2006 | Stover et al. |
| 2006/0064332 A1 | 3/2006 | Schoenbaum et al. |
| 2006/0076400 A1 | 4/2006 | Fletcher |
| 2006/0080144 A1 | 4/2006 | Goel et al. |
| 2006/0085335 A1 | 4/2006 | Crawford et al. |
| 2006/0113376 A1 | 6/2006 | Reed et al. |
| 2006/0143052 A1 | 6/2006 | Fotsch et al. |
| 2006/0149595 A1 | 7/2006 | Williams et al. |
| 2006/0149670 A1 | 7/2006 | Nguyen et al. |
| 2006/0167720 A1 | 7/2006 | Harrison et al. |
| 2006/0173777 A1 | 8/2006 | Torres et al. |
| 2006/0253324 A1 | 11/2006 | Miller |
| 2006/0277075 A1 | 12/2006 | Salwan |
| 2006/0287914 A1 | 12/2006 | Shelley |
| 2007/0005402 A1 | 1/2007 | Kennedy |
| 2007/0007335 A1 | 1/2007 | Cracchiolo et al. |
| 2007/0011088 A1 | 1/2007 | Cracchiolo et al. |
| 2007/0011089 A1 | 1/2007 | DeSchryver |
| 2007/0023504 A1 | 2/2007 | Blankenship et al. |
| 2007/0033070 A1 | 2/2007 | Beck et al. |
| 2007/0106607 A1 | 5/2007 | Seib et al. |
| 2007/0119920 A1 | 5/2007 | Hogg et al. |
| 2007/0168279 A1 | 7/2007 | D'Angelo |
| 2007/0175985 A1 | 8/2007 | Barnes et al. |
| 2007/0179813 A1 | 8/2007 | Darling |
| 2007/0185799 A1 | 8/2007 | Harrison et al. |
| 2007/0185800 A1 | 8/2007 | Harrison et al. |

| | | |
|---|---|---|
| 2007/0185801 A1 | 8/2007 | Harrison et al. |
| 2007/0185802 A1 | 8/2007 | Harrison et al. |
| 2007/0185803 A1 | 8/2007 | Harrison et al. |
| 2007/0194108 A1 | 8/2007 | Kalappa et al. |
| 2007/0194109 A1 | 8/2007 | Harrison et al. |
| 2007/0203757 A1 | 8/2007 | Dibiasi et al. |
| 2007/0265961 A1 | 11/2007 | Shah et al. |
| 2008/0011820 A1 | 1/2008 | Brown et al. |
| 2008/0110971 A1 | 5/2008 | Pover et al. |
| 2008/0156868 A1 | 7/2008 | Slen et al. |
| 2008/0179395 A1 | 7/2008 | Dixon et al. |
| 2008/0195423 A1 | 8/2008 | Baylor et al. |
| 2008/0210751 A1 | 9/2008 | Kim |

OTHER PUBLICATIONS

Hall, The profitability of vertical mergers between hospitals and physician practices, Journal of Health Economics, vol. 18, Issue 5, Oct. 1999, pp. 621-652.*

Hall, The profitability of vertical mergers between hospitals and physician practices, Journal of Health Economics, vol. 18, Issue 5, Oct. 1999, pp. 621-665.*

Chan et al., U.S. Appl. No. 11/674,437, filed Feb. 13, 2007, entitled "Methods, Systems, and Computer Program Products for Promoting Healthcare Information Technologies to Card Members".

Haase et al., U.S. Appl. No. 11/770,367, filed Jun. 28, 2007, entitled "Universal Rollover Account".

Harrison et al., U.S. Appl. No. 11/698,955, filed Jan. 29, 2007, entitled "Filtered Healthcare Payment Card Linked to Tax-Advantaged Accounts".

Jagatic et al., U.S. Appl. No. 11/561,326, filed Dec. 17, 2006, entitled "Variable Revenue Sharing for Multiple Account Payment Instruments".

Jagatic et al., U.S. Appl. No. 11/675,478, filed Feb. 15, 2007, entitled "Transmission and Capture of Line-Item-Detail to Assist in Transaction Substantiation and Matching".

Keck et al., U.S. Appl. No. 11/675,438, filed Feb. 15, 2007, entitled "Practice Management System (PMS) Integration".

Keck et al., U.S. Appl. No. 11/675,456, filed Feb. 15, 2007, entitled "Practice Management System (PMS) Integration".

Keck et al., U.S. Appl. No. 11/768,708, filed Jun. 26, 2007, entitled "Accelerated Payments for Health Care Plans".

Schoenberg, "Internet Based Repository of Medical Records That Retains Patient Confidentiality," *British Medical Journal*, vol. 321, Issue 7270, pp. 1199-1203 (Nov. 11, 2000).

Richardson, P., "Online broker woos real estate agents; Amerihall's fees lower than those of brick-and-mortar firms," Highbeam Research, Oct. 30, 2000, printed from http:www.highbeam.com/doc/1G1-66668508.html, 4 pages.

Bell, A., "Web Sites Push Medical Services Shopping. (Brief Article)," National Underwriter Property & Casualty-Risk & Benefits Management, Aug. 21, 2000, printed from http://www.highbeam.com/doc/1G1-65106694.html, 4 pages.

Harrison et al., U.S. Appl. No. 12/558,386, filed Sep. 11, 2009, entitled "Healthcare Card Incentive Program for Multiple Users".

Office Communication, dated Feb. 26, 2009, for U.S. Appl. No. 11/381,641, filed May 4, 2006, 12 pages.

Notice of Allowance, dated Aug. 6, 2009, for U.S. Appl. No. 11/381,641, filed May 4, 2006, 6 pages.

Office Communication, dated Mar. 10, 2009, for U.S. Appl. No. 11/275,399, filed Dec. 29, 2005, 6 pages.

Office Communication, dated Oct. 5, 2009, for U.S. Appl. No. 11/275,399, filed Dec. 29, 2005, 9 pages.

Office Communication, dated May 8, 2009, for U.S. Appl. No. 11/275,401, filed Dec. 29, 2005, 5 pages.

Office Communication, dated Oct. 14, 2009, for U.S. Appl. No. 11/275,401, filed Dec. 29, 2005, 8 pages.

Office Communication, dated Oct. 6, 2006, for U.S. Appl. No. 11/275,405, filed Dec. 29, 2005, 5 pages.

Office Communication, dated May 1, 2007, for U.S. Appl. No. 11/275,405, filed Dec. 29, 2005, 11 pages.

Office Communication, dated Nov. 13, 2007, for U.S. Appl. No. 11/275,405, filed Dec. 29, 2005, 11 pages.

Notice of Allowance, dated Jun. 12, 2008, for U.S. Appl. No. 11/275,405, filed Dec. 29, 2005, 7 pages.

Office Communication, dated Jun. 15, 2006, for U.S. Appl. No. 10/904,639, filed Nov. 19, 2004, 8 pages.

Notice of Allowance, dated Dec. 28, 2006, for U.S. Appl. No. 10/904,639, filed Nov. 19, 2004, 6 pages.

Office Communication, dated Sep. 2, 2008, for U.S. Appl. No. 11/461,365, filed Jul. 31, 2006, 7 pages.

Office Communication, dated Feb. 23, 2009, for U.S. Appl. No. 11/461,365, filed Jul. 31, 2006, 8 pages.

Office Communication, dated Jul. 14, 2009, for U.S. Appl. No. 11/461,365, filed Jul. 31, 2006, 7 pages.

Office Communication, dated Sep. 29, 2008, for U.S. Appl. No. 11/461,374, filed Jul. 31, 2006, 7 pages.

Office Communication, dated Feb. 26, 2009, for U.S. Appl. No. 11/461,374, filed Jul. 31, 2006, 8 pages.

Office Communication, dated Jul. 15, 2009, for U.S. Appl. No. 11/461,374, filed Jul. 31, 2006, 11 pages.

Office Communication, dated Apr. 27, 2009, for U.S. Appl. No. 11/461,389, filed Jul. 31, 2006, 5 pages.

Notice of Allowance, dated Sep. 18, 2009, for U.S. Appl. No. 11/461,389, filed Jul. 31, 2006, 6 pages.

Office Communication, dated Jun. 20, 2008, for U.S. Appl. No. 11/461,392, filed Jul. 31, 2006, 17 pages.

Notice of Allowance, dated May 14, 2009, for U.S. Appl. No. 11/461,392, filed Jul. 31, 2006, 7 pages.

Office Communication, dated Sep. 4, 2008, for U.S. Appl. No. 11/461,394, filed Jul. 31, 2006, 13 pages.

Office Communication, dated May 26, 2009, for U.S. Appl. No. 11/461,394, filed Jul. 31, 2006, 15 pages.

Office Communication, dated Aug. 3, 2009, for U.S. Appl. No. 11/461,394, filed Jul. 31, 2006, 2 pages.

Office Communication, dated Jul. 2, 2008, for U.S. Appl. No. 11/461,396, filed Jul. 31, 2006, 26 pages.

Office Communication, dated Feb. 5, 2009, for U.S. Appl. No. 11/461,396, filed Jul. 31, 2006, 10 pages.

Office Communication, dated Jul. 27, 2009, for U.S. Appl. No. 11/461,396, filed Jul. 31, 2006, 25 pages.

Office Communication, dated Oct. 27, 2009, for U.S. Appl. No. 11/461,396, filed Jul. 31, 2006, 2 pages.

Office Communication, dated Sep. 26, 2007, for U.S. Appl. No. 11/675,438, filed Feb. 15, 2007, 9 pages.

Office Communication, dated Mar. 13, 2008, for U.S. Appl. No. 11/675,438, filed Feb. 15, 2007, 14 pages.

Office Communication, dated Jul. 6, 2009, for U.S. Appl. No. 11/768,708, filed Jun. 26, 2007, 14 pages.

Office Communication, dated Jan. 23, 2008, for U.S. Appl. No. 11/675,478, filed Feb. 15, 2007, 8 pages.

Office Communication, dated Aug. 11, 2008, for U.S. Appl. No. 11/675,478, filed Feb. 15, 2007, 9 pages.

Office Communication, dated Nov. 17, 2008, for U.S. Appl. No. 11/675,478, filed Feb. 15, 2007, 3 pages.

Office Communication, dated Mar. 31, 2009, for U.S. Appl. No. 11/675,478, filed Feb. 15, 2007, 9 pages.

Office Communication, dated Oct. 27, 2009, for U.S. Appl. No. 11/675,478, filed Feb. 15, 2007, 9 pages.

Office Communication, dated Jul. 20, 2009, for U.S. Appl. No. 11/698,955, filed Jan. 29, 2007, 6 pages.

Office Communication, dated Sep. 27, 2007, for U.S. Appl. No. 11/675,456, filed Feb. 15, 2007, 9 pages.

Office Communication, dated Mar. 13, 2008, for U.S. Appl. No. 11/675,456, filed Feb. 15, 2007, 11 pages.

Office Communication, dated Oct. 29, 2008, for U.S. Appl. No. 11/770,367, filed Jun. 28, 2007, 6 pages.

Office Communication, dated Jan. 6, 2009, for U.S. Appl. No. 11/770,367, filed Jun. 28, 2007, 21 pages.

Office Communication, dated Jun. 10, 2009, for U.S. Appl. No. 11/770,367, filed Jun. 28, 2007, 21 pages.

Office Communication, dated Oct. 7, 2009, for U.S. Appl. No. 11/770,367, filed Jun. 28, 2007, 2 pages.

Notice of Allowance, dated Nov. 30, 2009, for U.S. Appl. No. 11/381,641, filed May 4, 2006, 7 pages.

Office Communication, dated Dec. 1, 2009, for U.S. Appl. No. 11/461,374, filed Jul. 31, 2006, 11 pages.
Office Communication, dated Nov. 10, 2009, for U.S. Appl. No. 11/698,955, filed Jan. 29, 2007, 17 pages.
"Cybear Group Reports Third Quarter 2001 Results of Operations," Business Editors & Health/Medical/Technology Writers, Business Wire, New York, p. 1 (Oct. 25, 2001).
Fisher, Jean P., "Cary, N.C., Medical Technology Firm May Get Boost from Doctors' Endorsement," Knight Ridder Tribune Business News, Washington, p. 1 (Nov. 13, 2003).
"Health Savings Custodial Account Agreement," Trust Administrators, Inc., 1970 Broadway, Suite 1140, Oakland, California, downloaded from www.trustadmin.com/public_html/graphics/CustodialAgreement.pdf, 3 pages.
Office Communication, dated Jun. 4, 2010, for U.S. Appl. No. 11/381,641, filed May 4, 2006, 6 pages.
Office Communication, dated Mar. 17, 2010, for U.S. Appl. No. 11/461,356, filed Jul. 31, 2006, 13 pages.
Office Communication, dated Apr. 8, 2010, for U.S. Appl. No. 11/461,365, filed Jul. 31, 2006, 9 pages.
Office Communication, dated Jun. 8, 2010, for U.S. Appl. No. 11/461,374, filed Jul. 31, 2006, 14 pages.
Office Communication, dated Jun. 7, 2010, for U.S. Appl. No. 11/461,389, filed Jul. 31, 2006, 10 pages.
Office Communication, dated Feb. 5, 2010, for U.S. Appl. No. 11/461,394, filed Jul. 31, 2006, 12 pages.
Office Communication, dated May 12, 2010, for U.S. Appl. No. 11/461,396, filed Jul. 31, 2006, 27 pages.
Office Communication, dated Mar. 31, 2010, for U.S. Appl. No. 11/561,326, filed Nov. 17, 2006, 10 pages.
Office Communication, dated Dec. 24, 2009, for U.S. Appl. No. 11/674,437, filed Feb. 13, 2007, 7 pages.
Office Communication, dated Jun. 8, 2010, for U.S. Appl. No. 11/674,437, filed Feb. 13, 2007, 15 pages.
Office Communication, dated Apr. 20, 2010, for U.S. Appl. No. 11/675,478, filed Feb. 15, 2007, 9 pages.
Office Communication, dated Mar. 30, 2010, for U.S. Appl. No. 11/698,955, filed Jan. 29, 2007, 12 pages.
Office Communication, dated Jan. 26, 2010, for U.S. Appl. No. 11/768,708, filed Jun. 26, 2007, 14 pages.
Office Communication, dated Dec. 24, 2009, for U.S. Appl. No. 11/770,367, filed Jun. 28, 2007, 25 pages.
Office Communication, dated Jun. 24, 2010, for U.S. Appl. No. 11/770,367, filed Jun. 28, 2007, 25 pages.
Office Communication, dated May 21, 2010, for U.S. Appl. No. 12/558,386, filed Sep. 1, 2009, 15 pages.
Ruess, "Court Snarls MTF Claims Payment Now in Limbo"; [All Editions], Trenton Bureau, The Record, Bergen County, N.J.: Feb. 24, 1994, p. a.01.
Office Communication, dated Aug. 5, 2010, for U.S. Appl. No. 11/461,356, filed Jul. 31, 2006, 22 pages.
Breitkopf, D., "Card Issuers Jacking Up Phone Fees," American Banker, SourceMedia, Inc., Highbeam Research, printed Aug. 28, 2010 from <http://www.highbeam.com>, 2 pages (Publication Date: Jun. 30, 2003).
Office Communication, dated Sep. 10, 2010, for U.S. Appl. No. 11/461,394, filed Jul. 31, 2006, 13 pages.
Office Communication, dated Aug. 31, 2010, for U.S. Appl. No. 11/461,396, filed Jul. 31, 2006, 16 pages.
Office Communication, dated Sep. 1, 2010, for U.S. Appl. No. 11/561,326, filed Nov. 17, 2006, 7 pages.
Office Communication, dated Nov. 8, 2010, for U.S. Appl. No. 11/275,401, filed Dec. 29, 2005, 10 pages.
Notice of Allowance, dated Nov. 17, 2010, for U.S. Appl. No. 11/381,641, filed May 4, 2006, 7 pages.
Office Communication, dated Nov. 4, 2010, for U.S. Appl. No. 11/461,374, filed Jul. 31, 2006, 17 pages.
Notice of Allowance, dated Nov. 30, 2010, for U.S. Appl. No. 11/461,389, filed Jul. 31, 2006, 6 pages.
Office Communication, dated Nov. 15, 2010, for U.S. Appl. No. 11/561,326, filed Nov. 17, 2006, 7 pages.
Notice of Allowance, dated Dec. 21, 2010, for U.S. Appl. No. 11/674,437, filed Feb. 13, 2007, 8 pages.
Office Communication, dated Oct. 19, 2010, for U.S. Appl. No. 11/675,478, filed Feb. 15, 2007, 9 pages.
Office Communication, dated Jan. 5, 2011, for U.S. Appl. No. 11/770,367, filed Jun. 28, 2007, 27 pages.
Office Communication, dated Oct. 12, 2010, for U.S. Appl. No. 12/558,386, filed Sep. 1, 2009, 19 pages.
Office Communication, dated Nov. 8, 2010, for U.S. Appl. No. 11/275,401, filed Dec. 29, 2005, 10 pages.
Notice of Allowance, dated Nov. 17, 2010, for U.S. Appl. No. 11/381,641, filed May 4, 2006, 7 pages.
Office Communication, dated Nov. 4, 2010, for U.S. Appl. No. 11/461,374, filed Jul. 31, 2006, 17 pages.
Notice of Allowance, dated Nov. 30, 2010, for U.S. Appl. No. 11/461,389, filed Jul. 31, 2006, 6 pages.
Office Communication, dated Nov. 15, 2010, for U.S. Appl. No. 11/561,326, filed Nov. 17, 2006, 7 pages.
Notice of Allowance, dated Dec. 21, 2010, for U.S. Appl. No. 11/674,437, filed Feb. 13, 2007, 8 pages.
Office Communication, dated Oct. 19, 2010, for U.S. Appl. No. 11/675,478, filed Feb. 15, 2007, 9 pages.
Office Communication, dated Oct. 12, 2010, for U.S. Appl. No. 12/558,386, filed Sep. 1, 2009, 19 pages.
Adams, D.L. et al., "Addressing medical coding and billing," *Journal of the National Medical Association*, Washington, D.C., vol. 94, No. 6, pp. 430-447 (Jun. 2002).
Office Communication, dated Feb. 25, 2011, for U.S. Appl. No. 11/461,356, filed Jul. 31, 2006, 22 pages.
Office Communication, dated Feb. 23, 2011, for U.S. Appl. No. 11/461,374, filed Jul. 31, 2006, 19 pages.
Office Communication, dated Feb. 14, 2011, for U.S. Appl. No. 11/768,708, filed Jun. 26, 2007, 12 pages.

* cited by examiner

FACILITATING PAYMENTS TO HEALTH CARE PROVIDERS

CROSS-REFERENCE TO RELATED APPLICATIONS

This application claims benefit under 35 U.S.C. §119(e) to U.S. Provisional Patent Application No. 60/697,514, filed Jul. 8, 2005, which is incorporated by reference herein in its entirety.

BACKGROUND OF THE INVENTION

1. Field of the Invention

The present invention generally relates to a healthcare savings account and payment system and, more particularly, to a system and a method for administering card-based healthcare savings account and provider payment plans.

2. Related Art

Fundamental changes are occurring in the healthcare industry with respect to expenditures by consumers. Healthcare expenditures in the U.S. are expected to increase from approximately $558 B in 1988 to approximately $3,361 B by 2013. It is projected that consumers will pay a larger share of those expenditures, from approximately 14% in 2001 to an expected 19% in 2010.

Section 125 of the United States Internal Revenue Code offers tax savings to employees for medical, dependent care and childcare expenses. Likewise, Section 132 of the United States Internal Revenue Code offers employees tax savings for work-related parking and transportation expenses. For example, employees may be entitled to tax benefits if the employees withhold a portion of their payroll to pay for medical, dependent care, childcare, work-related parking expenses and/or work-related transportation expenses. In other words, the employees' payroll is taxed on the amount left after the withheld portion is subtracted from the payroll amount and the withheld portion is placed into a flexible spending account.

How consumers pay for healthcare expenditures also is changing. Presently, less than 20% of consumer healthcare payments is through use of "plastic," which includes debit cards, charge cards, and credit cards. This percentage is expected to grow by over 10% in five years to approximately 30% by 2010.

Another fundamental change that is expected to occur in the healthcare industry is the increase in use of consumer-directed healthcare plans ("CDHPs"), which offer tax advantages to employers who offer such plans and, for some CDHPs, to employees as well. Three CDHPs of most interest include: the Flexible Spending Account ("FSA"); the Health Savings Account ("HSA"); and the Healthcare Reimbursement Arrangement ("HRA"). These different CDHPs are discussed in more detail below.

The shift towards CDHPs, while providing tax and other benefits to employers and/or employees, also entails significant administrative costs borne by the employers. These costs include, for example, the costs associated with maintaining individual accounts for each participating employee. Additionally, providers of healthcare goods/services often encounter significant delays in payment from CDHPs, due to the amount of time necessary to substantiate receipts and to determine the respective payment responsibilities of the insurers and the employees.

Given the foregoing, what is needed is a system and a method for administering CDHPs which minimize the administrative costs of employers and which facilitates the process for paying providers.

BRIEF SUMMARY OF THE INVENTION

The present invention meets the above-identified needs by providing a system and computer-implemented method to facilitate a purchase comprising: receiving, at a first host computer, a request from a provider for payment authorization for a charge to a purchaser; examining a database coupled to the first host computer for information concerning the purchaser; providing the information concerning the purchaser to a second host computer associated with the provider; receiving at the first host computer information from a third host computer concerning a negotiated amount of the charge to the purchaser; tendering payment of the negotiated charge to the provider; and withdrawing an amount no greater than the negotiated amount of the charge from an account of the cardmember.

BRIEF DESCRIPTION OF THE DRAWINGS/FIGURES

The features and advantages of the present invention will become more apparent from the description set forth below when taken in conjunction with the drawings in which like reference numbers indicate identical or functionally similar elements.

Figure 2:
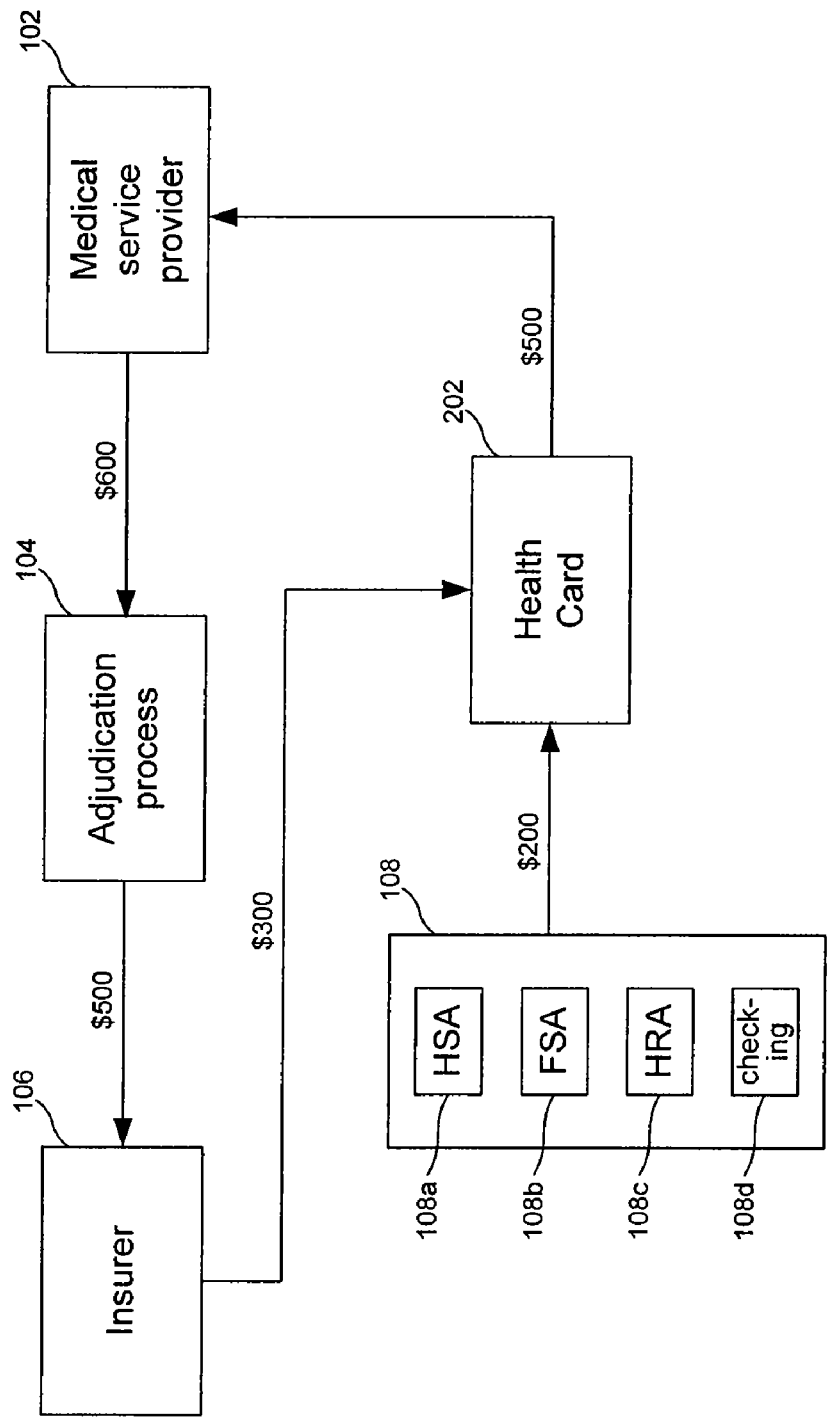
Figure 3:
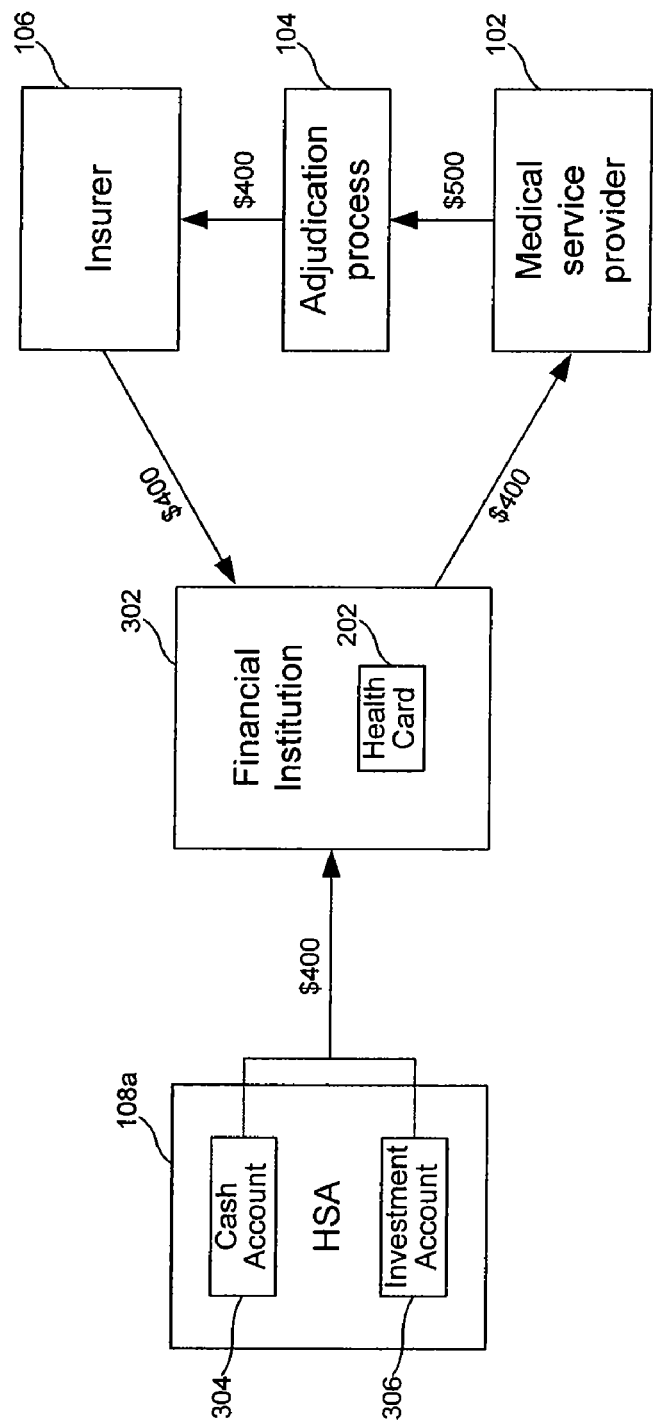
Figure 4:
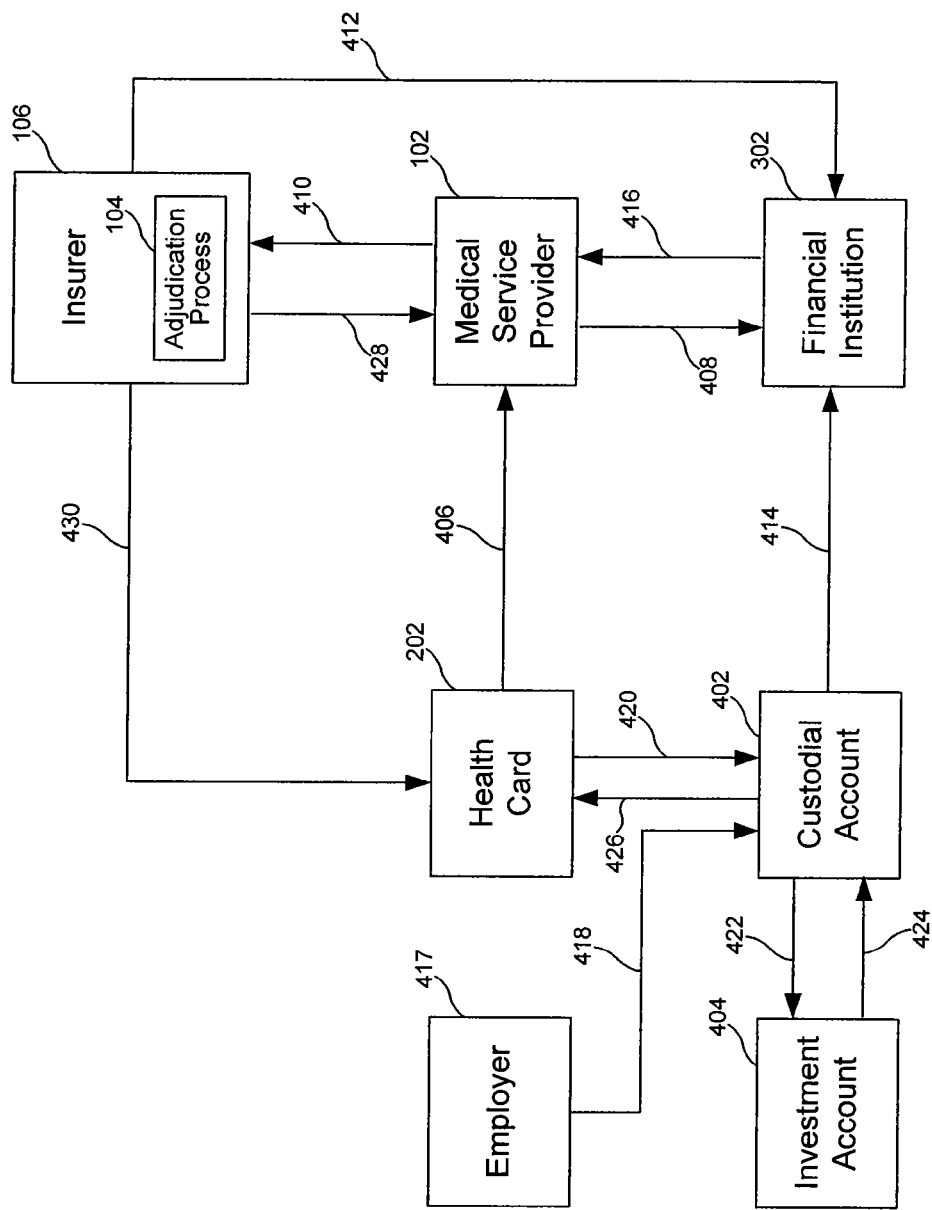
Figure 5:
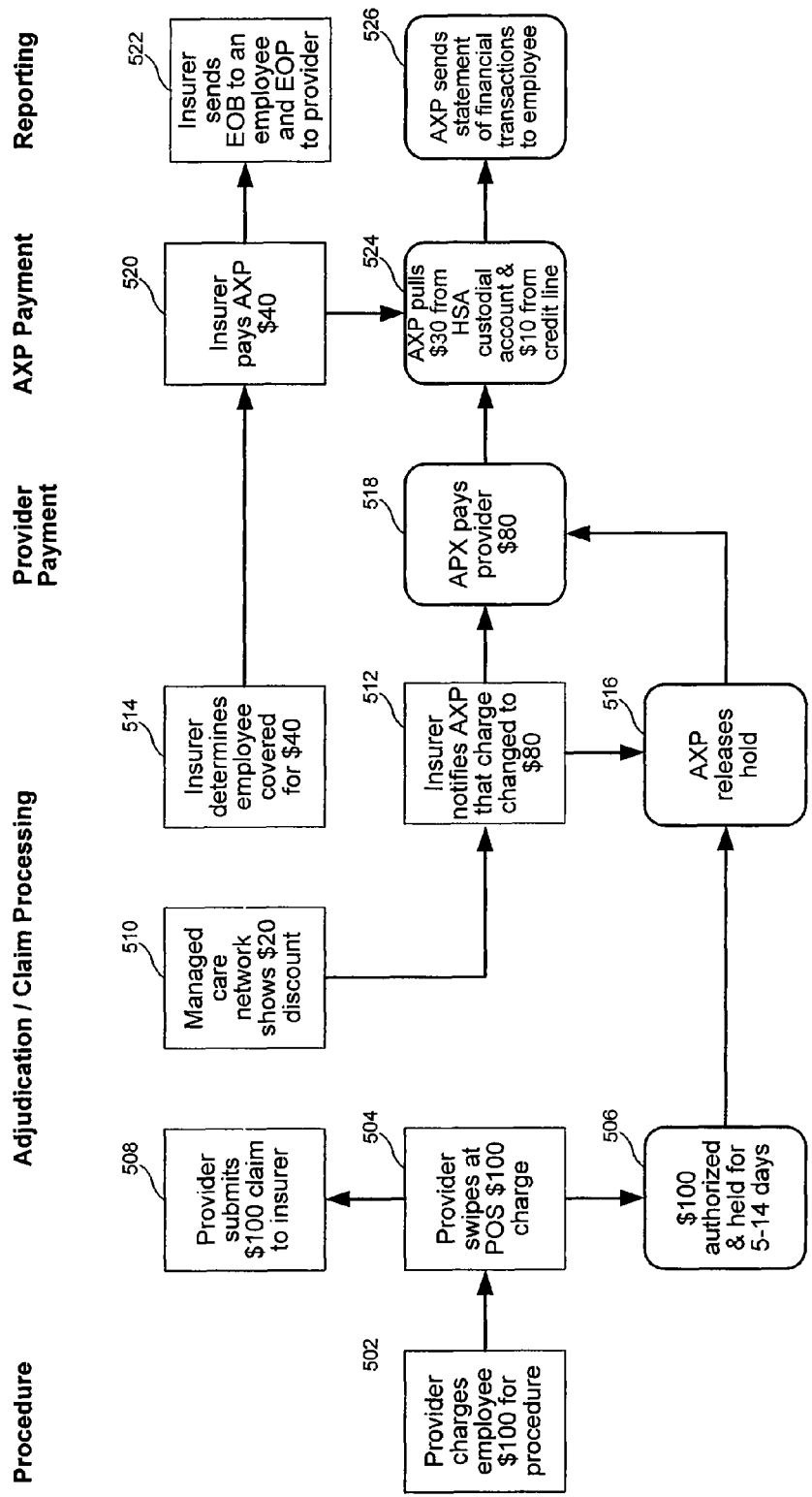
Figure 6:
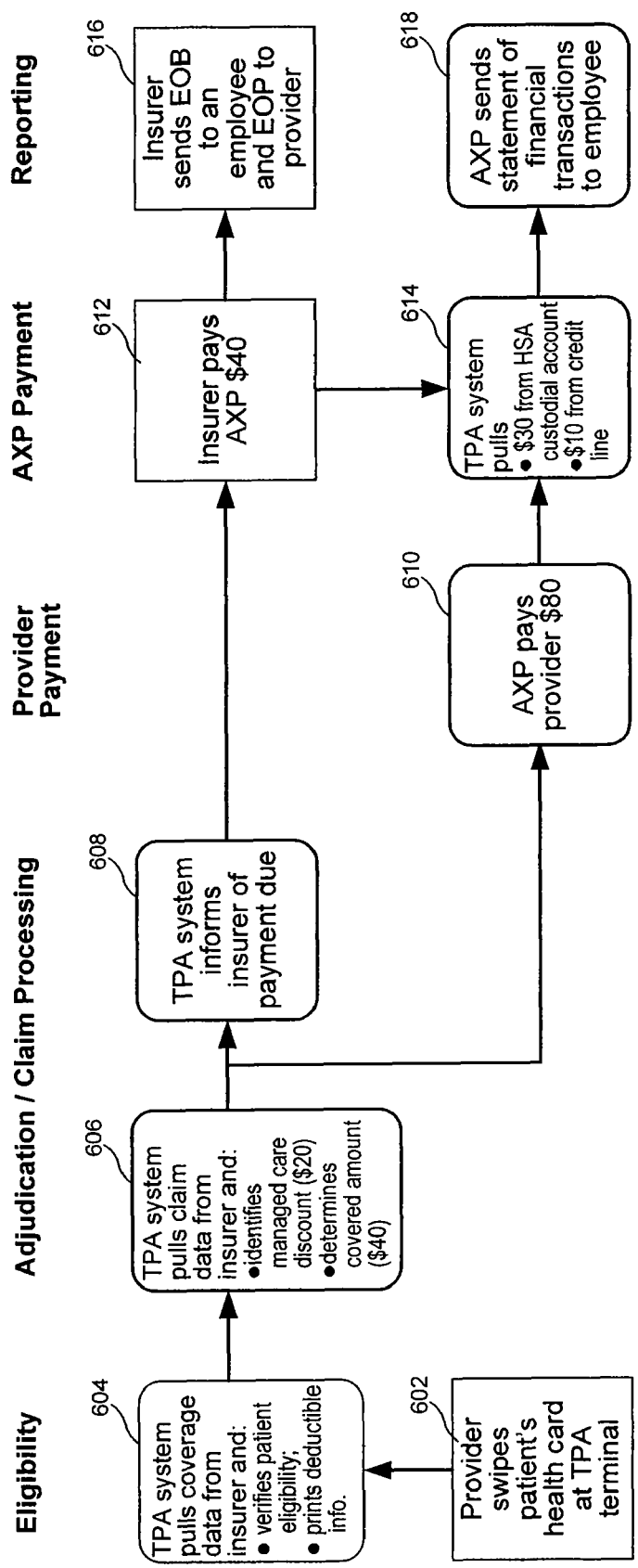
Figure 7:
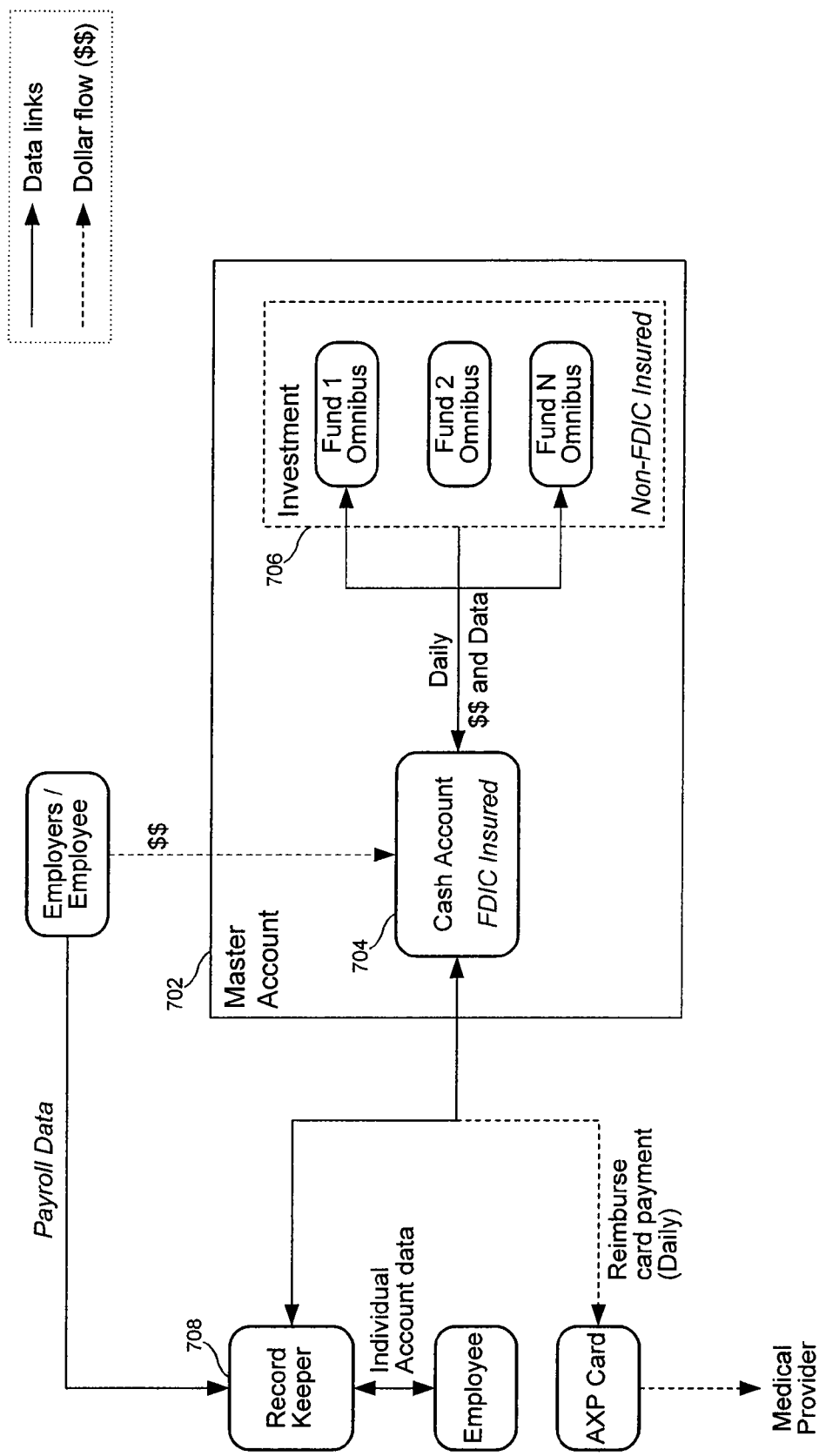
Figure 8:
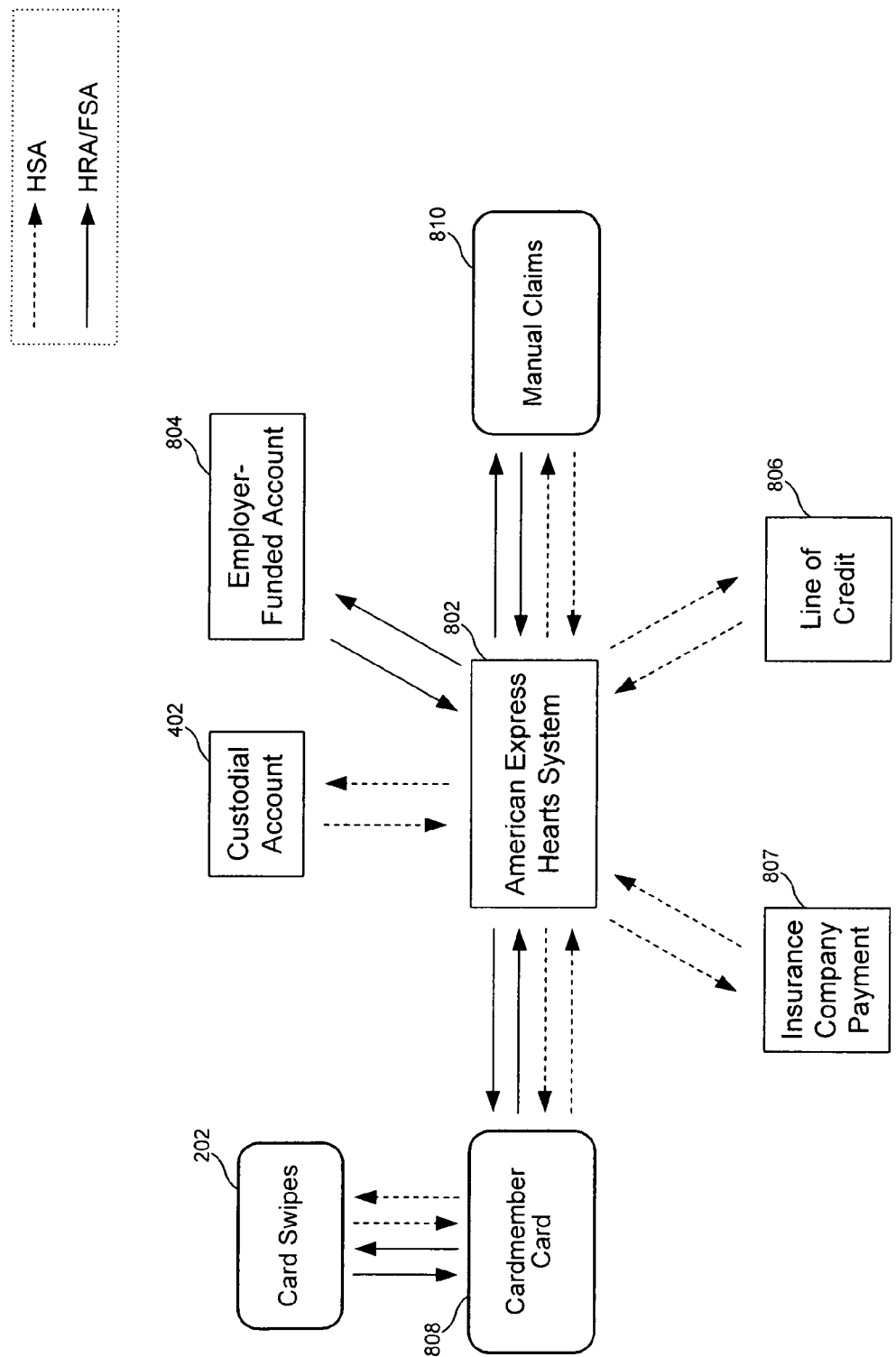
Figure 9:
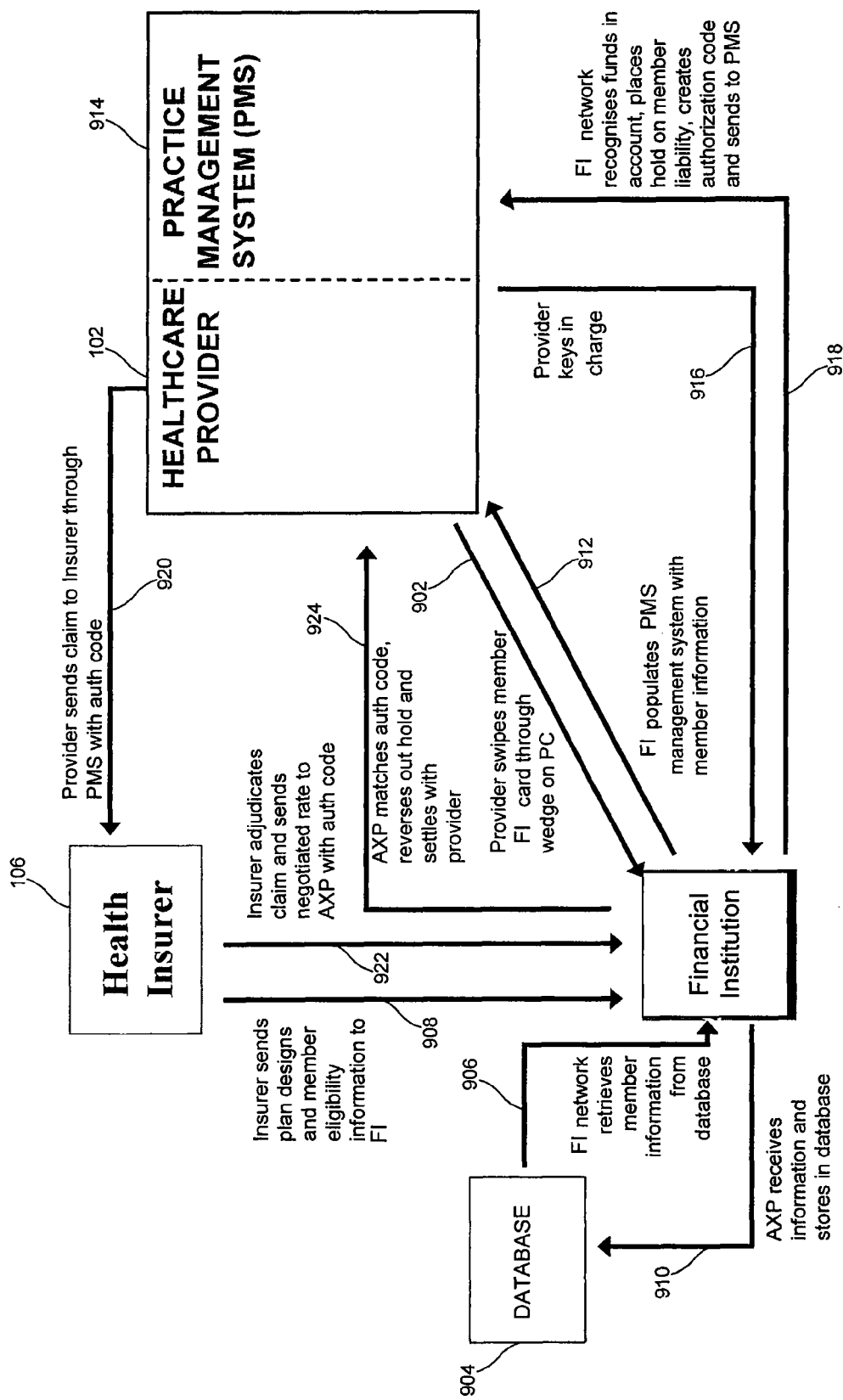
Figure 10:
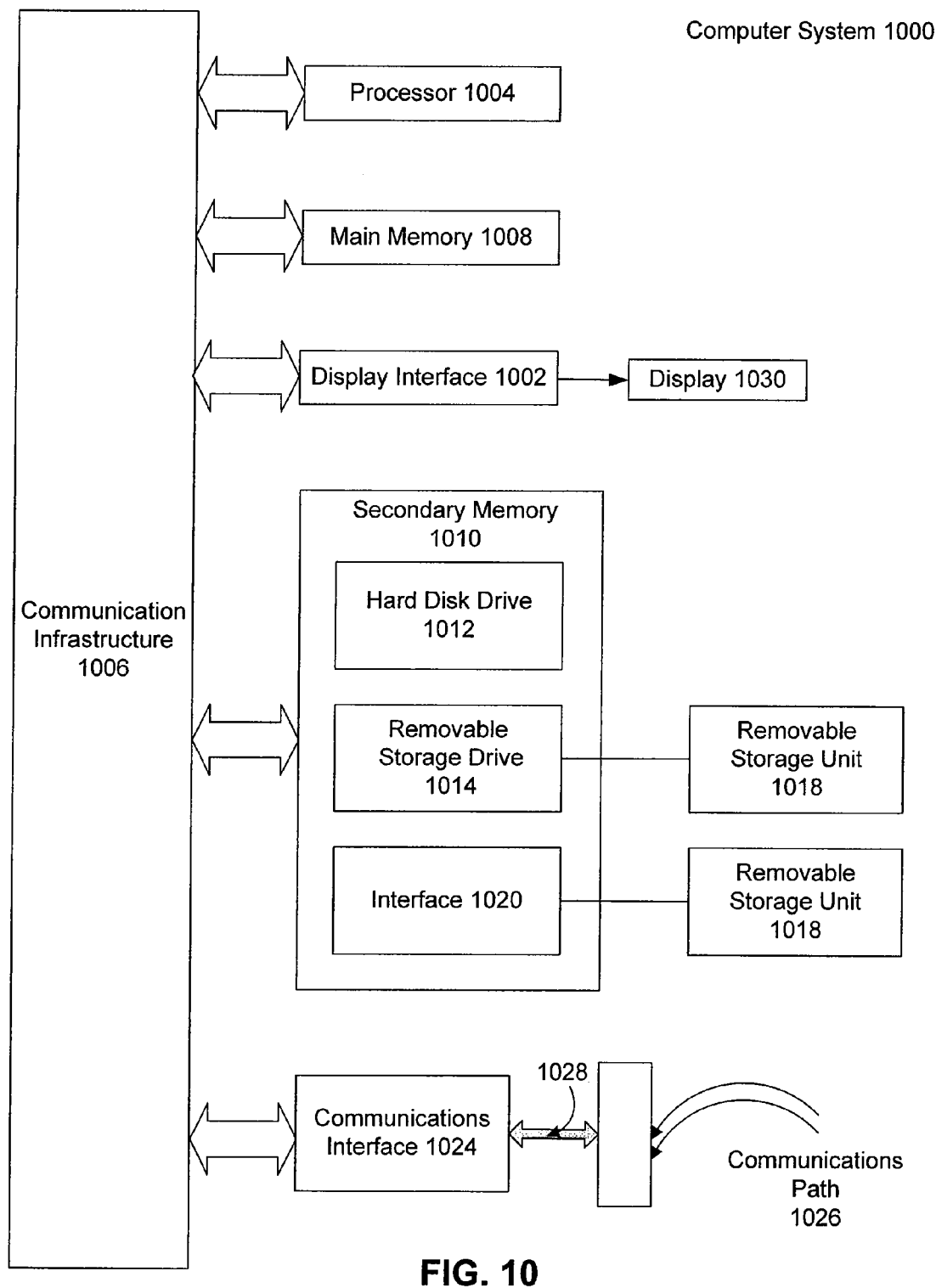

FIG. 1 schematically shows a conventional payment process;

FIG. 2 shows a payment process according to an embodiment of the present invention;

FIG. 3 schematically illustrates an example of a payment process flow according to an embodiment of the present invention;

FIG. 4 schematically illustrates another example of a payment process flow according to an embodiment of the present invention;

FIG. 5 schematically illustrates an example of various steps performed by a provider, an insurer, and a financial institution in connection with a payment process according to an embodiment of the present invention;

FIG. 6 schematically illustrates another example of various steps performed by a provider, an insurer, and a third party administrator in connection with a payment process according to an embodiment of the present invention;

FIG. 7 schematically illustrates an arrangement used by an employer to implement a CDHP according to an embodiment of the present invention;

FIG. 8 schematically illustrates a communication arrangement of a computer-based system according to an embodiment of the present invention;

FIG. 9 schematically illustrates an embodiment of the present invention implemented using a closed-loop network (as it relates to healthcare); and FIG. 10 is a block diagram of an exemplary computer system useful for implementing the present invention.

DESCRIPTION OF THE INVENTION

While specific configurations and arrangements are discussed, it should be understood that this is done for illustrative purposes only. A person skilled in the pertinent art will recognize that other configurations and arrangements can be used without departing from the spirit and scope of the present invention. It will be apparent to a person skilled in the pertinent art that this invention can also be employed in a variety of other applications.

Terminology

The term "merchant" as used herein shall mean any person, entity, distributor system, software, and/or hardware that is a provider, broker, and/or any other entity in the distribution chain of goods or services. For example, a merchant may be a credit card issuer, a hotel chain, an airline, a grocery store, a retail store, a travel agency, a service provider, including, but not limited to, a medical service provider, an online merchant, or the like.

A "transaction account" as used herein refers to an account associated with an open account card or a closed account card system (as described below). The transaction account may exist in a physical or non-physical embodiment. For example, a transaction account may be distributed in non-physical embodiments such as an account number, frequent-flyer account, telephone calling account or the like. Furthermore, a physical embodiment of a transaction account may be distributed as a financial instrument.

"Open cards" are financial transaction cards that are generally accepted at different merchants. Examples of open cards include the American Express®, Visa®, MasterCard® and Discover® cards, which may be used at many different retailers and other businesses. In contrast, "closed cards" are financial transaction cards that may be restricted to use in a particular store, a particular chain of stores or a collection of affiliated stores. One example of a closed card is a card that may only be accepted at a clothing retailer, such as a Saks Fifth Avenue® store.

The term "transaction instrument" as used herein may include any type of open or closed charge card, credit card, debit card, FSA card, stored value card, an RFID chip based card or token, and the like. For convenience, a transaction instrument may be referred to as a "card."

An "account," "account number" or "account code", as used herein, may include any device, code, number, letter, symbol, digital certificate, smart chip, digital signal, analog signal, biometric or other identifier/indicia suitably configured to allow a consumer to access, interact with or communicate with a financial transaction system. The account number may optionally be located on or associated with any financial transaction instrument (e.g., rewards, charge, credit, debit, prepaid, telephone, embossed, smart, magnetic stripe, bar code, transponder, radio frequency card or payment statement).

Persons skilled in the relevant arts will understand the breadth of the terms used herein and that the exemplary descriptions provided are not intended to be limiting of the generally understood meanings attributed to the foregoing terms.

It is noted that references in the specification to "one embodiment", "an embodiment", "an example embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to effect such feature, structure, or characteristic in connection with other embodiments whether or not explicitly described.

Overview

The invention is an assured payment system used with the healthcare flexible spending account card (hereinafter the Healthcare card). The assured payment system allows the medical services provider to be confident that at the time of swiping the Healthcare card they will be paid for services rendered to the card holder. The assured payment system involves several external vendors or partners. A processor, a third party administrator, an insurance company, and the employer are all involved. Firstly, the insurance company sends plan design information to the financial institution to establish a funding algorithm or multiple algorithms depending on the number of plan offerings.

After providing the healthcare service, the provider swipes the healthcare card for the retail amount of the claim. The financial institution processes the charge by running the algorithm that accounts for the consumer's out of pocket exposure. This will vary depending on several variables including the deductible amount, coinsurance percentage, and out of pocket maximums. For the deductible amount, the system will assume this to be the out of network amount to be conservative. The insurer passes a daily feed including the deductible amount, and the coinsurance percentage is determined once the member deductible is met. This is based on the member's responsibility using out of network coinsurance amounts. The out of pocket maximum represents the maximum total member liability.

The transaction is approved or declined based on the total funds available on the card including the line of credit, the HSA balance, and the insurance company portion of the payment. The financial institution will query the HSA account balance in real-time during the swipe to confirm if funds are available. A hold is then placed on the funds in the financial institution's system. However, settlement does not occur at the medical service provider in the normal time period. Rather, the hold is extended, based on a mutually agreed upon time period with the insurance company, until the adjudicated claim information for the transaction is received from the insurance company. The settlement may occur for a discounted amount.

The provider sends the claim to the insurance company through their normal adjudication process. The insurance company processes the claim and sends a file to financial institution. The settlement is generated by matching the retail claim amount with the hold, including the initial authorization number for the transaction. The financial institution utilizes the following fields as additional sources of verification for the transaction: member name and ID number, the date of the claim, location or zip code of the provider's office, and Tax ID number of the provider.

On matching the claim, the financial institution reverses the original authorization and settles with the merchant based on the discounted claim amount or the retail charge subject to the UCR level for that service. The provider receives an explanation of payment from the insurance company that includes the discounted claim amount, the retail charge, and the claim number. The member receives an explanation of benefits from the insurance company including the retail claim amount, discounted amount paid to the provider, and the claim number. The provider's statement and the member's statement both will include the claim numbers referenced above and reflect the discounted amount paid.

The invention resolves the provider's issue of collections. This solution takes the physician or other medical service provider out of the collections process altogether. The provider is no longer billing and waiting for payment. The financial institution now handles the process of payments through this solution. In addition, the patient no longer needs to worry about being billed properly by the physician (as the assured payment solution provides assurance that they are only paying the amount that they are responsible for per their health plan).

In one example of a known solution to the collections problem, the patient visits the doctor's office. Upon checkout, the patient presents his/her HSA debit card for payment. The doctor swipes the 'debit' card to initiate immediate payment of the full retail charge amount from the patient's HSA balance (e.g. a $300 charge for a visit that has actually been negotiated by insurer as a $100 visit). The doctor submits the claim to the insurer for adjudication and processing. The insurer adjudicates the claim and the patient receives an Explanation of Benefits (EOB) stating that the adjudicated amount for the visit is actually $100. The patient then needs to initiate contact with the doctor's office to resolve the overpayment issue (e.g. to seek reimbursement of $200). The doctor's office then has to credit the patient's HSA account or issue a reimbursement check. If the patient is issued a reimbursement check, the patient then needs to endorse the check and deposit it back into his/her HSA account.

In a second example of a known solution to the collections problem, the patient visits the doctor's office and, following instructions from Insurer, does not pay the doctor at the time of the visit, waiting instead for notice of adjudication process completion. The physician submits the claim to the insurer for adjudication and processing. The insurer adjudicates the claim. The patient receives an Explanation of Benefits (EOB) and the doctor receives an Explanation of Payment (EOP), stating that the adjudicated amount for the visit is actually $100. The doctor's office must then invoice the patient for the $100 owed. Doctors often have to send numerous invoices as medical bills are not prioritized for payment by many patients—after typically the third invoice, bills are sent to collections agencies. When the patient does pay, he/she must either write a check from the HSA account or go to the doctor's office to swipe his/her HSA debit card.

In the solution offered by the present invention, the patient visits the doctor's office. Upon checkout, the patient presents the financial institution's healthcare card for payment of the visit. A card swipe by the doctor's office initiates authorization but not payment of the charge based upon an algorithm that calculates the estimated patient liability and available amounts in one or more funding buckets. The physician submits the claim to the insurer for adjudication and processing. The insurer adjudicates the claim and the financial institution receives notification from the insurer stating that the member liability for the visit is $100. The financial institution initiates and completes payment to the physician from the appropriate funding "bucket" for the member's liability portion ($100).

Further details of embodiments of this invention are described below.

Embodiments

In a typical FSA, which is the most established of the CDHPs, an employer deducts pre-tax dollars from an employee's paycheck to cover IRS-approved healthcare expenses, and the deducted amount is put in the employee's FSA. The employee pays for healthcare goods and/or healthcare services ("goods/services") out of pocket, and submits a receipt for the goods/services for substantiation and reimbursement. A TPA reviews the receipt and confirms the purchase of the goods/services. Once confirmed, the TPA sends a reimbursement check to the employee and the TPA is reimbursed by the employer. Funds in the FSA that are not used by the employee by the end of the year are forfeited to the employer. TPAs have begun to offer debit cards to employees for payment of healthcare goods/services. These debit cards enable automation of some aspects of claims substantiation.

An HSA works in conjunction with an insurer's health insurance plan, which incorporates employee-paid deductibles. An employer and/or an employee contributes pre-tax dollars to the employee's HSA to cover IRS-approved healthcare expenses. The contributions are allowed to roll over from year to year and to accumulate tax free indefinitely. Funds in the HSA may be transferred from an investment account to a cash account to pay for expenses. When an HSA card or an HSA check is given to a provider for payment of healthcare goods/services, the provider submits a claim to the insurer. The insurer then determines the employee's share of the payment, withdraws the determined amount from the employee's cash account, and records that amount as part of the employee's deductible.

In a typical HRA, an employer contributes pre-tax dollars to an employee's HRA. Funds in the HRA may be used to pay for deductibles and/or out-of-pocket medical expenses, and may be used to replace existing healthcare benefits. The employer is allowed to determine factors such as: whether substantiation is required; an allowable annual roll-over amount; whether the HRA is to be fully funded at the beginning of the year; and particular goods/services that are not covered. The employee pays for healthcare goods/services out of pocket, and sends in a receipt for the goods/services for reimbursement, which is from funds in the HRA.

FIG. 1 schematically shows a conventional payment process, which is compared with a payment process according to an embodiment of the present invention, as shown in FIG. 2. Although the following description refers to the use of an HSA, the present invention may be practiced with an FSA or an HRA or any combination of the three types of CDHP accounts.

As shown in FIG. 1, in the conventional process, a provider (e.g., a doctor) 102 submits a claim for adjudication. For example, the claim may be for services rendered for an employee in the amount of $600. The adjudication process 104 makes a determination of the amount that the services are worth. In the current example, the claim for $600 is adjudicated to be worth $500. The employee's insurer 106 is notified of the adjudicated amount and, in turn, the insurer pays its share of the responsibility for the adjudicated amount to provider 102. For example, if the employee has an unpaid $200 deductible or if the insurer is responsible for 60% of the adjudicated amount, then the insurer pays the amount of $300 to the provider. Provider 102 then sends the employee an invoice for the unpaid portion of the adjudicated amount. The employee then pays the provider using funds from his/her account 108, typically comprising one or more of an HSA 108*a*, an FSA 108*b*, an HRA 108*c*, or a private account 108*d*.

FIG. 2 illustrates an aspect of the present invention in which the process of paying the provider is streamlined by use of a health card 202. Health card 202 is administered by a financial institution, which coordinates contributions from the insurer 106 and the employee's account 108.

FIG. 3 schematically illustrates an example of a payment process flow according to an embodiment of the present invention. In the illustrated example, an employee visits medical service provider 102 for a $500 procedure. The employee uses health card 202 to pay for the procedure. Health card 202 is administered by a financial institution 302 (e.g., American Express Co., Inc., of New York, N.Y. or "AXP"). Provider 102 files a claim for the service. Adjudication process 104 determines the value of the service to be $400. Insurer 106 identified by health card 202 is notified and sends financial institution 302 information on the claim and the adjudicated rate. Financial institution 302 obtains funds to pay for the adjudicated rate from insurer 106 and/or from the employee's HSA 108a. Preferably, HSA 108a includes a cash account 304 as well as an investment account 306. In the example of FIG. 3, the employee is responsible for the entire adjudicated rate of $400. However, if each of the insurer and the employee are responsible for a portion of the adjudicated rate, the financial institution would obtain funds from each responsible party in amounts corresponding to their respective portions. Financial institution 302 then sends the obtained funds to provider 102.

FIG. 4 schematically illustrates another example of a payment process flow according to an embodiment of the present invention. In the illustrated example, an employee visits provider 102 and uses health card 202 to pay for services rendered at step 406. Health card 202 is administered by financial institution 302. Provider 102 swipes health card 202, which initiates a communication to financial institution 302 at step 408 to perform an authorization process and to withhold payment until authorization is granted. Provider 102 also files a claim at step 410 with insurer 106 identified by health card 202, and insurer 106 adjudicates the claim to be worth an adjudicated amount. Insurer 106 then transfers its share of the adjudicated amount at step 412 to financial institution 302, along with other information regarding the claim and/or the employee, such as the claimed amount, the adjudicated amount, the employee's remaining deductible amount, etc. Financial institution 302 obtains funds to pay for the employee's share of the adjudicated amount by accessing at step 414 a custodial account 402 set up for the employee. Financial institution 302 settles the claim of provider 102 at step 416 using funds from insurer 106 and funds from the employee's custodial account 402.

Custodial account 402 is a CDHP account and is a cash account that is funded by employer 417 contributions at step 418 and/or contributions from the employee at step 420. In accordance with applicable laws and regulations, the employee contributions may be made via pre-tax payroll deductions. Any unused funds in the custodial account may be rolled over or transferred at step 422 into an investment account 404. When funds are necessary for payment of an adjudicated amount, funds may be transferred back into custodial account 402 at step 424 from investment account 404. Custodial account 402 is administered by a custodian, which may or may not be associated with financial institution 302. In one embodiment, investment account 404 is administered by financial institution 302. The custodian periodically provides the employee with a statement of financial transactions at step 426 involving custodial account 402. Optionally, insurer 106 may send reports at step 428 to provider 102 explaining payments for claims, and may send reports at step 430 to employees explaining bills to their CDHP accounts.

According to an aspect of the present invention, provider 102 sends a claim for the retail charge to insurer 106 for adjudication processing. Insurer 106 processes the claim and sends a file to financial institution 302.

A settlement is generated by matching the retail charge with a hold placed on the cardmember's account in the amount of the retail charge, including an initial authorization number for the transaction (when available). Optionally, financial institution 302 may use the following fields as additional sources of verification for the transaction: cardmember/employee name and ID number, date of the claim, location (e.g., zip code of the provider's office), and Tax ID number of the provider.

On matching the claim, financial institution 302 reverses the original authorization and settles with provider 102 for the discounted (adjudicated) claim amount or the retail charge subject to other adjustments, if warranted.

Provider 102 receives an explanation of payment ("EOP") from insurer 106 that includes the discounted claim amount, the retail charge, and claim number. The cardmember/employee receives an explanation of benefits ("EOB") from insurer 106 including the retail claim amount, the discounted amount paid to provider 102, and the claim number. The provider's statement and the member's statement both will include the claim numbers referenced above and reflect the discounted amount paid.

FIG. 5 schematically illustrates an example of the steps performed by provider 102, insurer 106, and financial institution 302 (referred to as "AXP" in FIG. 5) in connection with a payment process. In this example, provider 102 has performed a service or procedure for the employee, and the cost of the procedure is $100. Because provider 102 is a member of a network of providers associated with the insurer, there is a 20% discount on the cost of the procedure. The employee is covered by insurer 106 for 50% of the cost of the procedure, and the employee has $30 in her HSA 108a.

As shown in FIG. 5, provider 102 charges the employee $100 for the procedure at step 502, which the employee pays using her health card 202. Provider 102 swipes health card 202 at step 504 using a point-of-sale ("POS") device, such as those commonly used by merchants for registering payments made with credit/debit cards, and the provider enters the charge of $100 on the POS device. A code on the health card is automatically read, either electrically, magnetically, optically, or a combination thereof. Optionally, as is well known in the art, if the code cannot be automatically read by the POS device, a numeric code on health card 202 can be manually entered on the POS device by provider 102. The charge of $100 undergoes authorization processing and financial institution 302 holds payment for a period of time (e.g., five to fourteen days) at step 506. Provider 102 also submits a claim for $100 to insurer 106 at step 508.

At step 510, insurer 106 determines that provider 102 is "in-network" and therefore the claim is entitled to a 20% discount, i.e., the adjudicated amount to be paid to the provider is $80. At step 512, insurer 106 notifies financial institution 302 of the adjudicated amount and also determines that the employee is responsible for 50% of the adjudicated amount, or $40, at step 514. Financial institution 302 releases the hold on the payment at step 516 and pays provider 102 $80 at step 518. Insurer 106 pays financial institution 302 for its share of the adjudicated amount (i.e., $40) at step 520, and sends a report at step 522 to provider 102 explaining the payment of the adjudicated amount. Insurer 106 also sends a report at step 522 to the employee explaining her share of the adjudicated amount, which is to be billed to her HSA 108a. The employee's HSA 108a has $30 in cash, so financial institution 302 accesses HSA 108a at step 524 to obtain the $30 and also obtains the remaining $10 from a credit line associated with the employee. Financial institution 302 sends a report to the employee at step 526 explaining the financial transactions that occurred.

Optionally, some of the steps performed by the insurer and the financial institution may be performed by an external party, referred to as a TPA, as shown in FIG. 6. At step 602, provider 102 swipes the employee's health card 202 on a TPA POS terminal, in a similar manner as described above. At step 604, the TPA system verifies the employee's eligibility and determines deductible information. At step 606, the TPA system pulls claim data from insurer 106, identifies the managed care discount and determines the covered amount. At step 608, the TPA system notifies insurer 106 of the amount of payment. At the same time, at step 610, the TPA notifies financial institution 302 to pay provider 102 $80. At step 612, insurer 106 pays financial institution 302 the covered amount ($40). At step 614, the TPA system withdraws $30 from the employee's HSA 108a and $10 from the employee's credit line. At step 616, insurer 106 sends a report to provider explaining the payment of the adjudicated amount and to the employee explaining her share of the adjudicated amount. At step 618, financial institution 302 sends a statement of the financial transactions to the employee.

One of the advantages of associating an investment account with a CDHP account is that such an association provides the employee with flexibility in how funds designated for healthcare are managed. That is, the employee has control over whether the funds are maintained as cash or are invested in stocks, bonds, and/or other types of securities, which have the potential to grow in value.

FIG. 7 schematically illustrates an arrangement used by an employer to implement a CDHP according to an embodiment of the present invention. As shown in FIG. 7, the employer maintains a Master Account 702 in which all the funds for the employees are aggregately held. The Master Account includes a cash account 704, which is FDIC insured, and an investment account 706, which is not FDIC insured. The investment account allows for investment in a plurality of investment funds. Money and data are transferred between the cash account and the plurality of investment funds of the investment account on a periodic basis (e.g., hourly, daily, or weekly, etc.).

Funds in Master Account 702 are automatically obtained from the employees through payroll deduction and/or from the employer. A record keeper 708 maintains a record of each employee's individual CDHP account, including the allocation of the employee's funds to cash account 704 and investment account 706, as well as the allocation of the employee's investment-account funds to the plurality of investment funds.

The present invention may be implemented using a computer system, which interconnects the employer, the insurer 106, financial institution 302, the employees or a combination thereof, as schematically shown in FIG. 8. The illustrated "Hearts System" 802 is a centralized computer-based system that allows financial institution 302 to manage custodial accounts 402, employer-funded accounts 804, manual claims 810, lines of credit 806, payments 807 from insurers 106, "card swipes" (i.e., requests for payments from providers) 808, etc. That is, financial institution 302 facilitates the transfer of funds between multiple sources.

Hearts System 802 allows for the reconciliation of transactions from multiple funding sources with the use of a single health card 202. System 802 obtains funds from an appropriate funding source based on a hierarchy and a merchant/provider category code associated with each card. The various funding sources include any or all of an HSA 108a, an FSA 108b, an HRA 108c, line of credit 806, and a transit account 108d. The merchant/provider category code determines how an expense is allocated based on the merchant type. This allows for specific funding buckets to be used for dental goods/services, and different specific funding buckets to be used for vision goods/services, for example. According to an aspect of the present invention, these funding sources may be established as special purpose HRAs, FSAs, or benefits paid under "Section 132" for transportation benefits. In this instance the employer would fund an account for such transactions and the financial institution would allocate money for the transactions as they occur by pulling funds via an Automated Clearing House (ACH) arrangement.

Financial institution 302 pulls funds from the employee's CDHP account for transactions that should be debited from the CDHP account. Account numbers for the employees are stored in Hearts System 1002 to allow information to be passed to ACH funds.

Another funding source that is accessible by Hearts System 1002 is an employee's line of credit 1006 which may be underwritten by financial institution 302. According to the multiple-source funding arrangement of the present invention, financial institution 302 allows an employee ("cardmember") to opt to have his line of credit tapped first as a funding source before tapping the CDHP account, for those cardmembers who wish to maximize the tax benefits of the CDHP account as a savings vehicle.

Manual claims that are funded from the employer or individual accounts are sent to financial institution 302 prior to approval by insurer 106 or a TPA. This allows the financial institution to adjust the balance in the appropriate funding source, thus preventing accounts from becoming overdrawn.

To assure payment of providers, when insurer 106 and financial institution 302 get together to arrange a card-based payment plan according to the present invention, a funding algorithm or multiple algorithms are established depending on the number of plan offerings. After provider 102 provides a healthcare service, provider 102 swipes the employee's health card 202 using a POS-type device, for example, and inputs the retail amount of the claim or charge for the service. Financial institution 302 processes the charge by running the algorithm, which determines the employee's out-of-pocket exposure or payment responsibility based on a number of variables, including:

the employee's deductible amount;
 the coinsurance percentage once the employee's deductible is met; and
 an out-of-pocket maximum representing the maximum total liability of the employee.

A transaction is approved or declined based on the total funds available on the employee's health card, which takes into account the following: a line of credit, if approved; the HSA, if the member elects to include that as part of the bucket of funds for payment; and the insurer's portion of the payment. In one example, the financial institution queries the account balance of the HSA in real time during or immediately after the swipe to confirm whether funds are available. The financial institution places a hold on the funds, and settlement may not occur in the customary time period for ordinary retail merchants. The hold may be extended, based on a mutually agreed upon time period with the insurer, until the adjudicated claim information for the transaction is received from the insurer. Also, settlement may occur for a discounted amount and not for the fully amount claimed.

According to an embodiment, the present invention is implemented using a closed-loop network (as it relates to healthcare), the financial institution owns and manages the network, and the financial institution is the issuing bank for the health cards. As such, the financial institution is able to assure payment of providers via this closed-loop network. Additionally, the financial institution is able to set rules specific to healthcare transactions at provider locations, including setting the amount of time that settlement may be extended while a claim is adjudicated and adjusting the treatment of card transactions submitted from the providers so a hold is placed on funds as assurance to the providers.

Optionally, the financial institution utilizes the closed-loop network to pass additional information along with the transaction, to assist in verifying member/employee eligibility for insurance coverage, for example, as well as data fields that will assist in matching a hold on funds with information on an adjudicated claim.

This aspect allows for both eligibility information and pre-population of fields from a provider's Practice Management (PM) system from a card swipe. In addition, it facilitates processing of payment to the provider and adjudication of claims. It allows for both real-time and batch processing of claims by estimating member liability (based on in or out-of network plan design information stored by the financial institution).

In the example shown in FIG. 9, following the rendering of service, provider 102 swipes the cardmember's card through a POS device. At step 902, the card number and other identifying information is transmitted to financial institution 302. At step 906, financial institution 302 retrieves the cardmember information from a database 904 maintained by financial institution 302. Database 904 contains cardmember information generated by financial institution 302 as well as health care plan data and cardmember eligibility information provided by insurer 106 at step 908 and stored in database 904 at step 910. At step 912, financial institution 302 sends the cardmember plan data and eligibility to a practice management system (PMS) 914 maintained by provider 102. At step 916, provider 102 keys in the charge for the service performed and sends the charge to financial institution 302. This charge may be a retail charge or it may be a charge based on the cardmember's plan data and eligibility information that was provided by financial institution 302 at step 912. Upon receipt of the charge information, financial institution 302 places a hold on the cardmember account in the amount of the charge and sends an authorization code associated with the transaction to PMS 914 at step 918. At step 920, PMS 914 transmits a claim in the amount of the charge to insurer 106 along with the authorization code associated with the transaction generated by financial institution 302. Insurer 106 adjudicates the claim and at step 922 sends the negotiated rate to financial institution 302 with the authorization code. Financial institution 302 matches the authorization code, reverses the hold on the cardmember's account and at step 924 settles with provider 102 for the negotiated amount.

This allows financial institution 302 to immediately determine how much of the negotiated amount to withdraw from the cardmember's account and how much is payable by insurer 106.

This aspect of the invention allows for real-time claim substantiation and adjudication. It eliminates the need for a paper Explanation of Payments and accelerates cash flow for providers. It also reduces operating costs for health plans and eliminates the need for eligibility determination via phone or web inquiry.

Others have tried web-enabled solutions that allow for processing of claims but do not incorporate settlement of transactions or provide alternative sources for settlement on a real-time basis (e.g., line of credit (LOC)). This aspect of the present invention allows for adjudication and settlement for traditional insurance products as well as Consumer Driven Health Care ("CDHC") products. By transmitting member and health plan data directly into the practice management system, a provider is able to identify at the time of service not only the correct negotiated rate through real time adjudication, but also the patient liability to appropriately charge the patient at the time of service.

If the health plan cannot provide updated pricing and deductible data to facilitate real-time adjudication, transmitting this information directly into the practice management system will assist the provider in electronic claims submission. By including the authorization code with the claim, this will facilitate the matching for the financial institution's assured payment process.

Another aspect of the invention involves incentives to the cardmember for using a health card. Specifically, the financial institution offers incentives to the cardmember for usage of a payment card that is linked to pre-tax accounts like healthcare FSAs or HRAs. Incentives are either structured based on usage of the card (per transaction) or based on the amount spent (per charge volume). These points would be accumulated over time, and when a certain threshold is reached they could be redeemed for specific goods or services. This concept can be further refined to offer varying levels of points based on eligible versus ineligible spend. This would be done through coordination between the card issuer and the TPA to share information regarding claims amounts processed for specific participants. Incentives are given at differing levels depending on the type of usage. For example, eligible spend that is automatically substantiated earns 2 points per $1 spent, eligible items that require manual substantiation earn 1 point per $1 spent, and ineligible spend earns 0 points. This feature helps to resolve the lack of correct usage of pre-tax programs by participants.

In fact, in one embodiment, the invention is directed toward one or more computer systems capable of carrying out the functionality described herein. An example of a computer system 1000 is shown in FIG. 8.

Computer system 1000 includes one or more processors, such as processor 1004. Processor 1004 is connected to a communication infrastructure 1006 (e.g., a communications bus, cross-over bar, or network). Various software embodiments are described in terms of this exemplary computer system. After reading this description, it will become apparent to a person skilled in the relevant art(s) how to implement the invention using other computer systems and/or architectures.

Computer system 1000 can include a display interface 1002 that forwards graphics, text, and other data from communication infrastructure 1006 (or from a frame buffer not shown) for display on display unit 1016.

Computer system 1000 also includes a main memory 1008, preferably random access memory (RAM), and may also include a secondary memory 1010. Secondary memory 1010 may include, for example, a hard disk drive 1012 and/or a removable storage drive 1014, representing a floppy disk drive, a magnetic tape drive, an optical disk drive, etc. Removable storage drive 1014 reads from and/or writes to a removable storage unit 1018 in a well known manner. Removable storage unit 1018 represents a floppy disk, magnetic tape, optical disk, etc. which is read by and written to by removable storage drive 1014. As will be appreciated, removable storage unit 1018 includes a computer usable storage medium having stored therein computer software and/or data.

In alternative embodiments, secondary memory 1010 may include other similar devices for allowing computer programs or other instructions to be loaded into computer system 1000. Such devices may include, for example, a removable storage unit 1022 and an interface 1020. Examples of such may include a program cartridge and cartridge interface (such as that found in video game devices), a removable memory chip (such as an erasable programmable read only memory (EPROM), or programmable read only memory (PROM)) and associated socket, and other removable storage units 1022 and interfaces 1020, which allow software and data to be transferred from removable storage unit 1022 to computer system 1000.

Computer system 1000 may also include a communications interface 1024. Communications interface 1024 allows software and data to be transferred between computer system 1000 and external devices. Examples of communications interface 1024 may include a modem, a network interface (such as an Ethernet card), a communications port, a Personal Computer Memory Card International Association (PCM-CIA) slot and card, etc. Software and data transferred via communications interface 1024 are in the form of signals 1028 which may be electronic, electromagnetic, optical or other signals capable of being received by communications interface 1024. These signals 1028 are provided to communications interface 1024 via a communications path (e.g., channel) 1026. This channel 1026 carries signals 1028 and may be implemented using wire or cable, fiber optics, a telephone line, a cellular link, an radio frequency (RF) link and other communications channels.

In this document, the terms "computer program medium" and "computer usable medium" are used to generally refer to media such as removable storage drive 1014, a hard disk installed in hard disk drive 1012, and signals 1028. These computer program products provide software to computer system 1000. The invention is directed to such computer program products.

Computer programs (also referred to as computer control logic) are stored in main memory 1008 and/or secondary memory 1010. Computer programs may also be received via communications interface 1024. Such computer programs, when executed, enable computer system 1000 to perform the features of the present invention, as discussed herein. In particular, the computer programs, when executed, enable processor 1004 to perform the features of the present invention. Accordingly, such computer programs represent controllers of computer system 1000.

In an embodiment where the invention is implemented using software, the software may be stored in a computer program product and loaded into computer system 1000 using removable storage drive 1014, hard drive 1012 or communications interface 1024. The control logic (software), when executed by processor 1004, causes processor 1004 to perform the functions of the invention as described herein.

In another embodiment, the invention is implemented primarily in hardware using, for example, hardware components such as application specific integrated circuits (ASICs). Implementation of the hardware state machine so as to perform the functions described herein will be apparent to persons skilled in the relevant art(s).

In yet another embodiment, the invention is implemented using a combination of both hardware and software.

While various embodiments of the present invention have been described above, it should be understood that they have been presented by way of example, and not limitation. It will be apparent to persons skilled in the relevant art(s) that various changes in form and detail can be made therein without departing from the spirit and scope of the present invention (e.g., packaging and activation of other transaction cards and/or use of batch activation processes). Thus, the present invention should not be limited by any of the above described exemplary embodiments, but should be defined only in accordance with the following claims and their equivalents.

In addition, it should be understood that the figures illustrated in the attachments, which highlight the functionality and advantages of the present invention, are presented for example purposes only. The architecture of the present invention is sufficiently flexible and configurable, such that it may be utilized (and navigated) in ways other than that shown in the accompanying figures.

Further, the purpose of the following Abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The Abstract is not intended to be limiting as to the scope of the present invention in any way.

What is claimed is:

1. A method comprising:
    receiving, using a computing device, information corresponding to a claim by a healthcare provider for services rendered to a patient;
    placing a hold, using the computing device, on at least one account of the patient, wherein the hold is placed for a mutually agreed upon time period between a financial institution and an insurer;
    receiving, using the computing device, a message from the insurer including information regarding a negotiated rate of the claim, an insurer portion of the claim, and an authorization code;
    matching, using the computing device, the authorization code with a stored code associated with the claim;
    releasing, using the computing device, the hold after receiving the message from the insurer;
    tendering payment, using the computing device and based at least in part on the message from the insurer, of a patient portion of the claim;
    determining, using the computing device, whether the claim requires manual processing or whether the claim can be processed automatically; and
    awarding, using the computing device, incentive points to an incentive points account of the patient based at least in part on whether the claim requires manual processing.

2. The method of claim 1, wherein sending of the information corresponding to the claim is initiated by a use of a health card to pay for the services rendered to the patient.

3. The method of claim 2, further comprising offering an incentive based on the use of the health card.

4. The method of claim 3, wherein the incentive is based on per transaction usage of the health card or based on a total amount spent.

5. The method of claim 2, wherein the computing device and the health card are owned and managed by a financial institution in a closed-loop network.

6. The method of claim 5, wherein the financial institution sets rules specific to healthcare transactions, including setting an amount of time that settlement may be extended during claim adjudication.

7. The method of claim 2, further comprising:
    retrieving patient information from a database based on the use of the health card.

8. The method of claim 1, wherein the health care provider is either an in-network health care provider or an out-of-network health care provider, and wherein the message includes discount information if the health care provider is an in-network health care provider.

9. The method of claim 1, wherein the at least one account of the patient comprises:
    a Flexible Savings Account (FSA);
    a Health Savings Account (HSA);
    a Healthcare Reimbursement Account (HRA);
    a savings account;
    a checking account; or
    a line-of-credit (LOC) account.

10. The method of claim 1, further comprising:
    associating the computing device with one or more of:

an insurance company;

a third party administrator (TPA); or a financial institution.

11. The method of claim 1, further comprising establishing one or more funding algorithms, based on plan design information, to control respective purchaser and insurance company liabilities for the claim.

12. The method of claim 1, further comprising:

verifying one or more of: a patient name, a patient identification number (ID), a date of the claim, a location of the health care provider, or a tax ID of the healthcare provider.

13. The method of claim 1, further comprising determining an estimated patient cost based on:

a deductible of the patient;

a coinsurance percentage once the deductible is met; or a maximum total liability of the patient.

14. The method of claim 1, wherein tendering payment comprises accessing a custodial account established for the patient by an employer of the patient.

15. The method of claim 1, wherein tendering payment comprises obtaining funds from an employee master account administered by an employer of the patient, and wherein the employee master account includes funds for a plurality of employees of the employer.

16. The method of claim 1, further comprising authorizing payment of the claim prior to settling the claim.

17. The method of claim 1, wherein the awarding further comprises:

awarding a first amount of incentive points to the incentive points account if the claim can be processed automatically; and awarding a second amount of incentive points to the incentive points account if the claim requires manual processing.

18. The method of claim 1, further comprising:

determining a first amount of incentive points to be awarded for claims that can be processed automatically; and determining a second amount of incentive points to be awarded for claims requiring manual processing.

19. An article of manufacture including a non-transitory computer-readable medium having instructions stored thereon, execution of which by a computing device causes the computing device to perform operations comprising:

receiving information corresponding to a claim by a healthcare provider for services rendered to a patient;

placing a hold on at least one account of the patient, wherein the hold is placed for a mutually agreed upon time period between a financial institution and an insurer;

receiving a message from the insurer including information regarding a negotiated rate of the claim, an insurer portion of the claim, and an authorization code;

matching the authorization code with a stored code associated with the claim;

releasing the hold after receiving the message from the insurer;

tendering payment, based at least in part on the message from the insurer, of a patient portion of the claim;

determining whether the claim requires manual processing or whether the claim can be processed automatically; and awarding incentive points to an incentive points account of the patient based at least in part on whether the claim requires manual processing.

20. An apparatus comprising:

a processor; and a memory storing instructions, execution of which by the processor causes the processor to:

receive information corresponding to a claim by a healthcare provider for services rendered to a patient;

place a hold on at least one account of the patient, the hold being placed for a mutually agreed upon time period between a financial institution and an insurer;

receive a message from the insurer including information regarding a negotiated rate of the claim, an insurer portion of the claim, and an authorization code;

match the authorization code with a stored code associated with the claim;

release the hold after receiving the message from the insurer;

tender payment, based at least in part on the message from the insurer, of a patient portion of the claim;

determine whether the claim requires manual processing or whether the claim can be processed automatically; and award incentive points to an incentive points account of the patient based at least in part on whether the claim requires manual processing.

* * * * *

UNITED STATES PATENT AND TRADEMARK OFFICE
CERTIFICATE OF CORRECTION

| | | |
|---|---|---|
| PATENT NO. | : 7,970,626 B2 | Page 1 of 1 |
| APPLICATION NO. | : 11/275403 | |
| DATED | : June 28, 2011 | |
| INVENTOR(S) | : Cracchiolo et al. | |

It is certified that error appears in the above-identified patent and that said Letters Patent is hereby corrected as shown below:

Title page, item (73), under "Assignee", in Column 1, Line 1, delete "Acquistitions" and insert -- Acquisitions --.

Signed and Sealed this
Twenty-fifth Day of October, 2011

David J. Kappos
*Director of the United States Patent and Trademark Office*